United States Patent
Savadjiev et al.

(10) Patent No.: US 11,257,210 B2
(45) Date of Patent: Feb. 22, 2022

(54) METHOD AND SYSTEM OF PERFORMING MEDICAL TREATMENT OUTCOME ASSESSMENT OR MEDICAL CONDITION DIAGNOSTIC

(71) Applicant: THE ROYAL INSTITUTION FOR THE ADVANCEMENT OF LEARNING/MCGILL UNIVERSITY, Montréal (CA)

(72) Inventors: Peter Savadjiev, Montréal (CA); Benoit Gallix, Montréal (CA); Kaleem Siddiqi, Westmount (CA)

(73) Assignee: THE ROYAL INSTITUTION FOR THE ADVANCEMENT OF LEARNING / MCGILL UNIVERSITY, Montréal (CA)

( * ) Notice: Subject to any disclaimer, the term of this patent is extended or adjusted under 35 U.S.C. 154(b) by 150 days.

(21) Appl. No.: 16/451,610

(22) Filed: Jun. 25, 2019

(65) Prior Publication Data
US 2019/0392579 A1    Dec. 26, 2019

Related U.S. Application Data

(60) Provisional application No. 62/848,649, filed on May 16, 2019, provisional application No. 62/689,467, filed on Jun. 25, 2018.

(51) Int. Cl.
*G06T 7/00* (2017.01)
*G16H 50/20* (2018.01)
(Continued)

(52) U.S. Cl.
CPC ............ *G06T 7/0012* (2013.01); *G06T 7/11* (2017.01); *G16H 30/40* (2018.01); *G16H 50/20* (2018.01);
(Continued)

(58) Field of Classification Search
CPC ..... G06K 2009/00738; G06K 9/00711; G06K 9/00718; G06K 2209/057; G06K 9/00671;
(Continued)

(56) References Cited

U.S. PATENT DOCUMENTS 6,535,623 B1 * 3/2003 Tannenbaum ............ G06T 7/12
382/128
9,704,262 B2   7/2017 Baloch et al.
(Continued)

FOREIGN PATENT DOCUMENTS

WO    2012113069 A1    8/2012
WO    2014113786 A1    7/2014

OTHER PUBLICATIONS

O'Connor, J. P., Aboagye, E. O., Adams, J. E., Aerts, H. J., Barrington, S. F., Beer, A. J., . . . & Buckley, D. L. (2017). Imaging biomarker roadmap for cancer studies. Nature reviews Clinical oncology, 14(3), 169.
(Continued)

*Primary Examiner* — Quan M Hua
(74) *Attorney, Agent, or Firm* — Norton Rose Fulbright Canada LLP; Alexandre Daoust

(57) ABSTRACT

There is described a computer-implemented method of performing medical treatment outcome assessment or medical condition diagnostic. The method generally has receiving a three-dimensional (3D) anatomical image representing a region of a body of a patient; generating a 3D invariant image by processing the 3D anatomical image based on an isophote structure invariant entity (e.g., mean curvature of isophotes, Gaussian curvature of isophotes); using an image processing unit, processing the 3D invariant image and generating an output based on said processing, the output being either: medical treatment outcome data indicative of an outcome assessment of a treatment received by said
(Continued)

patient; or medical condition diagnostic data indicative of a diagnostic of a medical condition of said patient.

23 Claims, 16 Drawing Sheets

(51) Int. Cl.
    *G16H 30/40*         (2018.01)
    *G06T 7/11*          (2017.01)
    *G06T 19/20*         (2011.01)
    *G06T 7/12*          (2017.01)

(52) U.S. Cl.
    CPC ............ *G06K 2209/05* (2013.01); *G06T 7/12* (2017.01); *G06T 19/20* (2013.01); *G06T 2207/10088* (2013.01); *G06T 2207/30004* (2013.01); *G06T 2210/41* (2013.01)

(58) Field of Classification Search
    CPC ........... G06K 9/00765; G06K 9/00771; G06K 2009/4666; G06K 9/52; G06K 9/6215; G06K 2209/05; G06K 2209/051; G06K 9/00342; G06K 9/00744; G06K 9/3233; G06K 9/46; G06K 9/6267; G06K 9/6268; G06K 9/6278; G06K 9/6282; G06F 16/71; G06F 16/735; G06F 16/285; G06F 16/51; G06F 16/783; G06F 16/7847; G06F 16/9566; G06N 20/00; G06N 20/10; G06N 20/20; G06N 3/08; G06N 5/00; G06N 5/025
    See application file for complete search history.

(56) References Cited

U.S. PATENT DOCUMENTS

| | | | |
|---|---|---|---|
| 2008/0080770 | A1 | 4/2008 | Mendonca et al. |
| 2008/0319308 | A1* | 12/2008 | Tang ..................... A61B 5/055 600/416 |
| 2012/0081386 | A1 | 4/2012 | Wiemker et al. |
| 2014/0073907 | A1* | 3/2014 | Kumar ............... A61B 10/0241 600/414 |
| 2015/0356730 | A1* | 12/2015 | Grove ....................... G06T 7/64 382/124 |
| 2017/0177812 | A1* | 6/2017 | Sjolund .................. G06N 20/00 |
| 2017/0193655 | A1 | 7/2017 | Madabhushi et al. |

OTHER PUBLICATIONS

Aerts, H. J., Velazquez, E. R., Leijenaar, R. T., Parmar, C., Grossmann, P., Carvalho, S., . . . & Hoebers, F. (2014). Decoding tumour phenotype by noninvasive imaging using a quantitative radiomics approach. Nature communications, 5, 4006.
Aerts, H. J. (2016) The potential of radiomic-based phenotyping in precision medicine: a review. JAMA oncology, 2 (12), 1636-1642.
Therasse, P., Arbuck, S. G., Eisenhauer, E. A., Wanders, J., Kaplan, R. S., Rubinstein, L., . . . & Gwyther, S. G. (2000). New guidelines to evaluate the response to treatment in solid tumors. Journal of the National Cancer Institute, 92(3), 205-216.
Chun, Y. S., Vauthey, J. N., Boonsirikamchai, P., Maru, D. M., Kopetz, S., Palavecino, M., . . . & Loyer, E. M. (2009). Association of computed tomography morphologic criteria with pathologic response and survival in patients treated with bevacizumab for colorectal liver metastases. Jama, 302(21), 2338-2344.
Giiflin, L. D , & Colchester, A. C (1995) Superficial and deep structure in linear diffusion scale space: Isophotes, critical points and separatrices. Image and Vision Computing, 13(7), 543-557.
Koenderink, J. J. (1984). The structure of images. Biological cybernetics, 50(5), 363-370.
Kuijper, A., & Florack, L. M. (2004). The relevance of non-generic events in scale space models. International Journal of Computer Vision, 57(1), 67-84.
Koenderink, J. J., & van Doorn, A. J. (1980). Photometric invariants related to solid shape. Optica Acta: International Journal of Optics, 27(7), 981-996.
Maintz, J. B. A., van den Eisen, P. A., & Viergever, M. A. (1996). Evaluation of ridge seeking operators for multimodality medical image matching. IEEE Transactions on pattern analysis and machine intelligence, 18(4), 353-365.
Valenti, R., & Gevers, T. (Jun. 2008). Accurate eye center location and tracking using isophote curvature. In 2008 IEEE Conference on Computer Vision and Pattern Recognition (pp. 1-8). IEEE.
Lichtenauer, J., Hendriks, E., & Reinders, M. (Jun. 2005). Isophote properties as features for object detection. In 2005 IEEE Computer Society Conference on Computer Vision and Pattern Recognition (CVPR'05) (vol. 2, pp. 649-654). IEEE.
Poeschl, T. (1984). Detecting surface irregularities using isophotes. Computer Aided Geometric Design, 1(2), 163-168.
Theisel, H., & Farin, G. (1997). The curvature of characteristic curves on surfaces. IEEE Computer Graphics and Applications, 17(6), 88-96.
Chaware, L., Cannon, R., Kembhavi, A. K., Mahabal, A., & Pandey, S. K. (2014). Isophotal shapes of early-type galaxies to very faint levels. The Astrophysical Journal, 787(2), 102.
Monga, O., Ayache, N., & Sander, P. T. (1992). From voxel to intrinsic surface features. Image and Vision Computing, 10(6), 403-415.
Thirion, J. P., & Gourdon, A. (1995). Computing the differential characteristics of isointensity surfaces. Computer vision and image understanding, 61(2), 190-202.
Goldman, R. (2005). Curvature formulas for implicit curves and surfaces. Computer Aided Geometric Design, 22(7), 632-658.
Eberly, D., Gardner, R., Morse, B., Pizer, S., & Scharlach, C. (1994). Ridges for image analysis. Journal of Mathematical Imaging and Vision, 4(4), 353-373.
López, A. M., Lloret, D., Serrat, J., & Villanueva, J. J. (2000). Multilocal creaseness based on the level-set extrinsic curvature. Computer Vision and Image Understanding, 77(2), 111-144.
Florack, L. M., Romeny, B. T. H., Koenderink, J. J., & Viergever, M. A. (1994). General intensity transformations and differential invariants. Journal of Mathematical Imaging and Vision, 4(2), 171-187.

* cited by examiner

METHOD AND SYSTEM OF PERFORMING MEDICAL TREATMENT OUTCOME ASSESSMENT OR MEDICAL CONDITION DIAGNOSTIC

CROSS-REFERENCE TO RELATED APPLICATIONS

This application claims priority on both U.S. Provisional Application Ser. No. 62/689,467, filed on Jun. 25, 2018, and U.S. Provisional Application Ser. No. 62/848,649, filed on May 16, 2019, the entire contents of which are incorporated herein by reference.

FIELD

The improvements generally relate to medical imaging, and more particularly relates to anatomical image processing.

BACKGROUND

Medical imaging encompasses a number of techniques of creating visual representations of a region of a body of a patient for clinical analysis and medical intervention. Typically, medical imaging generally focuses on imaging internal structures hidden by the skin and bones of the patient in order to allow a skilled physician to diagnose and/or treat a medical condition.

For any given medical imaging technique, many types of medical imaging systems can be used, each producing anatomical images that can differ from one another in terms of imaging parameters such as brightness and contrast to name a few examples. Although existing medical imaging techniques and systems are satisfactory to a certain degree, there remains room for improvement, especially in analyzing anatomical images in a way that is not impacted by the respective imaging parameters of each of the anatomical images to analyze.

SUMMARY

It was found that as three-dimensional (3D) anatomical images may be analyzed to diagnose or treat a medical condition, such analysis may be inconveniently influenced by differences in the imaging parameters used to acquire the 3D anatomical images instead of being solely impacted by actual imaging biomarkers and/or biological abnormalities present in the 3D anatomical images.

It was found that, rather than analyzing the 3D anatomical images themselves to diagnose or treat a medical condition, the 3D anatomical images can be processed based on one or more isophote structure invariant properties such as a mean curvature of isophotes, a Gaussian curvature of isophotes and the like, to obtain invariant image(s) that are invariant to differences in imaging parameters used to acquire them. For instance, if a plurality of 3D anatomical images of the same region of the body of the patient are acquired with different imaging parameters, or simply with different units of a similar type of medical imaging system, the plurality of 3D anatomical images can be rendered similar to one another by processing them on the basis of the same isophote structure invariant entity. Then, by feeding one or more of these invariant image(s) to an image processing unit, the latter can process the invariant image(s) and generate an output indicative of medical treatment outcome data or medical condition diagnostic data in a manner which is not impacted by the respective imaging parameters of each of the anatomical images to analyze, thereby alleviating at least some of the aforementioned drawbacks.

In accordance with a first embodiment of the present disclosure, there is provided a computer-implemented method of performing medical treatment outcome assessment or medical condition diagnostic, the method comprising: receiving a three-dimensional (3D) anatomical image representing a region of a body of a patient; generating a 3D invariant image by processing the 3D anatomical image based on an isophote structure invariant entity; using an image processing unit, processing the 3D invariant image and generating an output based on said processing, the output being either: medical treatment outcome data indicative of an outcome assessment of a treatment received by said patient; or medical condition diagnostic data indicative of a diagnostic of a medical condition of said patient.

Further in accordance with the first embodiment, said isophote structure invariant entity is for example a mean curvature of isophotes.

Still further in accordance with the first embodiment, the mean curvature of isophotes is for example computed based on a formula:

$$\kappa = div\left(\frac{\nabla I}{\|\nabla I\|}\right),$$

wherein κ represents the mean curvature of isophotes, and/represents the image.

Still further in accordance with the first embodiment, an isophote is for example represented with an equation I(x,y,z)=c, wherein/is the image, c is a constant, and x, y and z are variables representing 3D spatial coordinates.

Still further in accordance with the first embodiment, the isophote structure invariant entity is for example a first isophote structure invariant entity and the 3D invariant image is a first 3D invariant image, the method further comprising generating for example a second 3D invariant image by processing the 3D anatomical image based on a second isophote structure invariant entity different from the first isophote structure invariant entity, said processing comprising processing the first and second 3D invariant images.

Still further in accordance with the first embodiment, the first isophote structure invariant entity is for example a mean curvature of isophotes and the second isophote structure invariant entity is for example a Gaussian curvature of isophotes.

Still further in accordance with the first embodiment, receiving for example data representative of treatment received by the patient, said processing being based on the 3D invariant data and on said data representative of treatment received by the patient.

Still further in accordance with the first embodiment, the image processing unit is for example a trained image processing unit.

Still further in accordance with the first embodiment, the 3D anatomical image comprises for example: a computed tomography (CT) image, a magnetic resonance imaging (MRI) image, a positron emission tomography (PET) scan image, or an ultrasound image.

Still further in accordance with the first embodiment, displaying for example said output via a user interface.

In accordance with a second embodiment of the present disclosure, there is provided a system for performing medical treatment outcome assessment or medical condition diagnostic, the system comprising: a processing device; and a non-transitory memory communicatively coupled to the processing device and comprising computer-readable program instructions executable by the processing device for: receiving a three-dimensional (3D) anatomical image representing a region of a body of a patient; generating a 3D invariant image by processing the 3D anatomical image based on an isophote structure invariant entity; using an image processing unit, processing the 3D invariant image and generating an output based on said processing, the output being either: medical treatment outcome data indicative of an outcome assessment of a treatment received by said patient; or medical condition diagnostic data indicative of a diagnostic of a medical condition of said patient.

Further in accordance with the second embodiment, said isophote structure invariant entity is for example a mean curvature of isophotes.

Still further in accordance with the second embodiment, the mean curvature of isophotes is for example computed based on a formula:

$$\kappa = div\left(\frac{\nabla I}{\|\nabla I\|}\right),$$

wherein κ represents the mean curvature of isophotes, and/represents the image.

Still further in accordance with the second embodiment, an isophote is for example represented with an equation I(x,y,z)=c, wherein I is the image, c is a constant, and x, y and z are variables representing 3D spatial coordinates.

Still further in accordance with the second embodiment, the isophote structure invariant entity is for example a first isophote structure invariant entity and the 3D invariant image is a first 3D invariant image, the method further comprising generating for example a second 3D invariant image by processing the 3D anatomical image based on a second isophote structure invariant entity different from the first isophote structure invariant entity, said processing comprising processing the first and second 3D invariant images.

Still further in accordance with the second embodiment, the first isophote structure invariant entity is for example a mean curvature of isophotes and the second isophote structure invariant entity is a Gaussian curvature of isophotes.

Still further in accordance with the second embodiment, receiving for example data representative of treatment received by the patient, said processing being based on the 3D invariant data and on said data representative of treatment received by the patient.

Still further in accordance with the second embodiment, the image processing unit is for example a trained image processing unit.

Still further in accordance with the second embodiment, the 3D anatomical image comprises for example: a computed tomography (CT) image, a magnetic resonance imaging (MRI) image, a positron emission tomography (PET) scan image, or an ultrasound image.

Still further in accordance with the second embodiment, a user interface communicatively coupled to said processing device displaying for example said output.

In accordance with a third embodiment of the present disclosure, there is provided a computer-implemented method for computing an imaging marker to monitor a patient treatment, the method comprising: receiving an image representing a region of a body of a patient; processing the image based on an isophote structure invariant entity of the image; computing a data set representative of the isophote structure invariant entity; receiving data representative of the patient treatment received by the patient; determining a likelihood of success of the patient treatment received by the patient based on the data set representative of the isophote structure invariant entity and the data representative of the patient treatment; and generating a signal based on said determined likelihood of success.

Further in accordance with the third embodiment, said patient treatment is for example a post-cancer treatment.

Still further in accordance with the third embodiment, said isophote structure invariant entity is for example a mean curvature of isophotes.

Still further in accordance with the third embodiment, the mean curvature of isophotes is for example computed based on a formula:

$$\kappa = div\left(\frac{\nabla I}{\|\nabla I\|}\right),$$

wherein κ represents the mean curvature of isophotes, and/represents the image.

Still further in accordance with the third embodiment, an isophote is for example represented with an equation I(x,y,z)=c, wherein I is the image, c is a constant, and x, y and z are variables representing 3D spatial coordinates.

Features of the systems, devices, and methods described herein may be used in various combinations, and may also be used for the system and computer-readable storage medium in various combinations.

Many further features and combinations thereof concerning the present improvements will appear to those skilled in the art following a reading of the instant disclosure.

DESCRIPTION OF THE FIGURES

In the figures, embodiments are illustrated by way of example. It is to be expressly understood that the description and figures are only for the purpose of illustration and as an aid to understanding.

Embodiments will now be described, by way of example only, with reference to the attached figures, wherein in the figures.

DETAILED DESCRIPTION

Disclosed herein includes systems and methods for performing medical treatment outcome assessment and/or medical condition diagnostic. In some embodiments, the systems and methods are used to monitor a patient's response to any suitable type of treatment that can be used to treat a medical condition. One example of such type of treatment includes a post-cancer treatment. For example, the systems and methods disclosed herein can monitor 3D anatomical images and generate 3D invariant images emphasizing an invariant structure hidden in the monitored 3D anatomical images which can be used to determine whether a treatment is effective, e.g., over a period of time for a patient. The systems and methods can monitor different types of medical condition by processing the 3D anatomical images using one or more isophote structure invariant properties of 3D anatomical images such as, but not limited to, a mean curvature of isophotes, a Gaussian curvature of isophotes and the like. The systems can be implemented as computer software programs, and can be applicable to any type of medical imaging modality, for instance including computerized tomography (CT) imaging, magnetic resonance imaging (MRI), or positron-emission tomography (PET). In some embodiments, the systems and methods described herein can include an image processing unit which is trained using machine learning (including, but not limited to deep learning) techniques, in which a large number of features may be computed from each 3D invariant images and are used to classify the 3D invariant images into different categories. For instance, the 3D invariant images may be classified into categories of predicted response (e.g., positive, negative, or neutral) and/or of medical condition diagnostic (e.g., ill, healthy).

It will be appreciated that numerous specific details are set forth in order to provide a thorough understanding of the exemplary embodiments described herein. However, it will be understood by those of ordinary skill in the art that the embodiments described herein can be practiced without these specific details. In other instances, well-known methods, procedures and components have not been described in detail so as not to obscure the embodiments described herein. Furthermore, this description is not to be considered as limiting to the scope of embodiments described herein in any way, but rather as merely describing implementation of the various example embodiments described herein.

Figure 1:
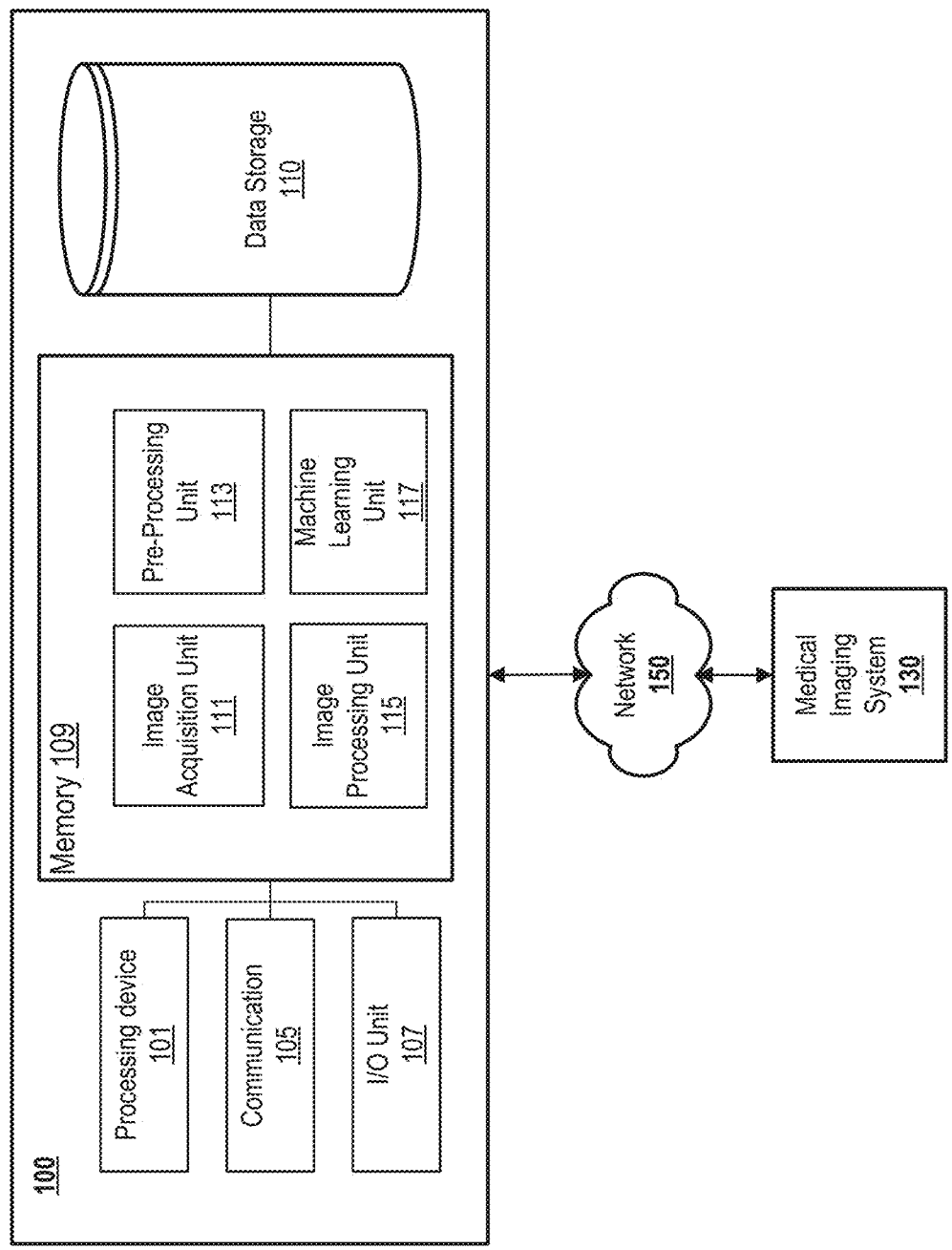
FIG. 1 is a schematic block diagram of an example system of performing medical treatment outcome assessment or medical condition diagnostic, in accordance with one or more embodiments.

Referring now to FIG. 1, which is a schematic block diagram of an example system 100 for performing medical treatment outcome assessment or medical condition diagnostic, according to some embodiments.

As depicted, system 100 has processing device 101 and non-transitory memory 109 communicatively coupled to the processing device 101. Memory 109 has stored thereon computer-readable program instructions which when executed by the processing device 101 perform a step of receiving 3D anatomical image representing a region of a body of a patient. A step of generating a 3D invariant image by processing the 3D anatomical image based on an isophote structure invariant entity. Using image processing unit 115, steps of processing the 3D invariant image and generating an output based on said processing, in which the output is indicative of medical treatment outcome data or medical condition diagnostic data. The medical treatment outcome data being indicative of an outcome assessment of a treatment received by said patient, whereas the medical treatment outcome data are indicative of a diagnostic of a medical condition of said patient.

In 3D image analysis, important information can be carried by geometric entities known as isophotes, or equivalently isocontours, i.e., curves or surfaces of equiluminance points. An isophote can thus be represented with an equation I(x,y,z)=c, wherein/is the image, c is a constant, and x, y and z are variables representing 3D spatial coordinates of the 3D anatomical image. These geometric entities are collectively referred to herein as isophote structure invariant entities and can correspond to visual features that are important in the real world, and can be therefore utilized for the semantic description of image content. For example, in computer vision, isophotes may play an important role in the analysis of image content at multiple scales of resolution, in what is known as scale space analysis. Examples of such isophote structure invariant entities can include, but not limited to, a mean curvature of isophote, a Gaussian curvature of isophotes and the like.

The isophote structure invariant entity on which the processing of the 3D anatomical images is based to generate 3D invariant images can be viewed as a property which render imperceptible at least some differences in imaging parameters such as brightness and contrast to name a few examples. The isophote structure invariant entity can thus be invariant to general invertible image transformations including, but not limited to, changes in brightness, changes in contrast. Invertible image transformations are such that the original 3D anatomical image can be recovered from the 3D transformed image, which implies that no informational content is lost through the image transformation. It can be shown that invertible image transformations are strictly monotonic, but no other restrictions are imposed on such invertible image transformations. For instance, the invertible image transformations can be highly non-linear. An example of a non-invertible image transformation is when a 3D anatomical image is transformed to a plain blank 3D image. In this scenario, the image transformation would not be invertible as all color or anatomical informational content would be lost, and the original image could not be retrieved from the blank image alone.

It is encompassed that the power of such isophote structure invariant entities can reside in their invariance to a vast array of image transformations. This invariance comes from the fact that these measures are not computed from absolute image pixel values, but may be rather functions of image derivatives. This invariance can make these measures a powerful pre-processing tool to be applied prior to machine learning. In case different radiological images have been acquired at different institutions, with different scanners using different parameters, it is quite likely that the radiological images will have systematic differences in appearance from one institution to the next. This is why computing these invariant measures on radiological images will help to extract information intrinsic to the tissue being imaged, and will be invariant to extrinsic factors such as changes in contrast, brightness and the like that may result from different scanning settings and that are not relevant to the biological question under investigation. This in turn can make machine learning a lot more robust and reliable. Instead of directly learning features of the original radiological images (which contain both intrinsic "signal" and extrinsic "noise"), machine learning can now learn features on the invariant images (such as the "mean curvature of isophotes" image, which contain more intrinsic "signal" and less extrinsic "noise"), which will result in machine learning models that can be more reproducible and more portable from one institution to another.

Figure 2A:
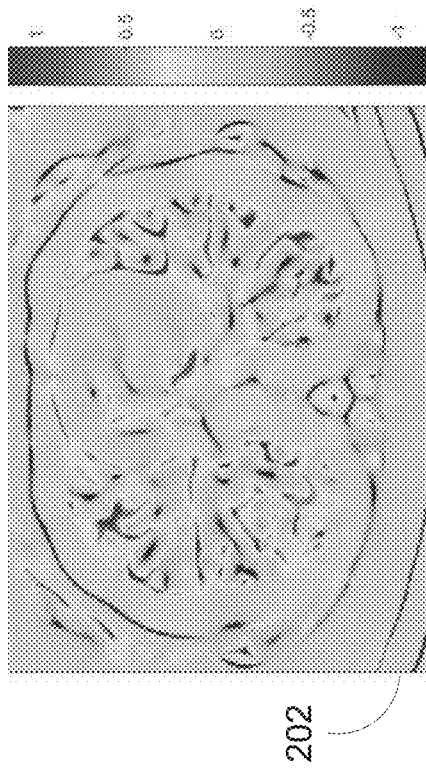
FIG. 2A is an example of a 3D anatomical image section showing a lung of a patient and acquired using first imaging parameters, in accordance with one or more embodiments.
Figure 2B:
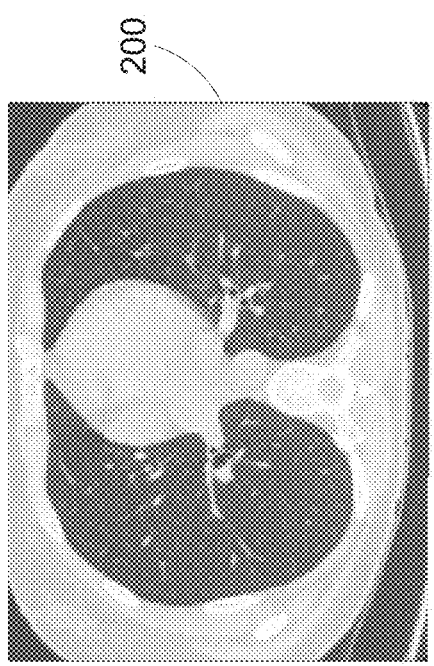
FIG. 2B is an example of a 3D invariant image section generated by processing the 3D anatomical image section of FIG. 2A based on a given isophote structure invariant entity, in accordance with one or more embodiments.
Figure 2C:
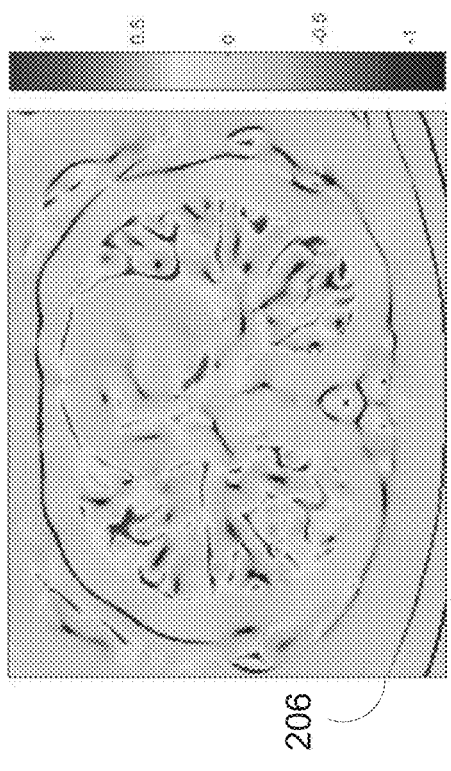
FIG. 2C is an example of a 3D anatomical image section showing a lung of a patient and acquired using second imaging parameters different from the first imaging parameters, in accordance with one or more embodiments.
Figure 2D:
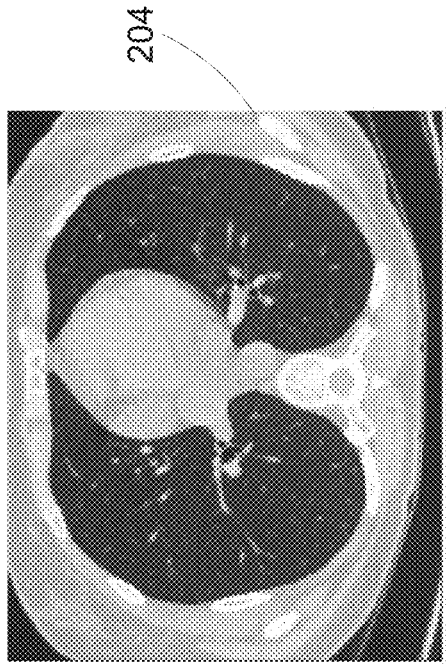
FIG. 2D is an example of a 3D invariant image section generated by processing the 3D anatomical image section of FIG. 2C based on the given isophote structure invariant entity, in accordance with one or more embodiments.

To illustrate such invertible image transformations, reference is now made to FIGS. 2A through 3D. As shown, FIG. 2A shows a 3D anatomical image section 200 of a lung of a patient and acquired using first imaging parameters. When the 3D anatomical image section 200 of FIG. 2A is processed on the basis of a given isophote structure invariant entity, 3D invariant image section 202 such as the one shown in FIG. 2B can be generated. FIG. 3C shows a 3D anatomical image section 204 showing the lung of the patient and acquired using second imaging parameters different from the first imaging parameters. For instance, 3D anatomical image sections 200 and 204 can be the same 3D anatomical image sections which have been post-processed to modify their respective brightness and/or contrast, or can be different 3D anatomical image sections of the same lung of the same patient taken at substantially the same moment in time but with different imaging parameters. When the 3D anatomical image section 204 of FIG. 2C is processed on the basis of the given isophote structure invariant entity, 3D invariant image section 206 such as the one shown in FIG. 2D can be generated. As can be appreciated, the 3D invariant image sections 202 and 206 are similar, even perhaps identical, to one another as they have been processed using the same isophote structure invariant entity.

It is intended that as image processing unit 115 of system 100 can be programmed, or even trained in some embodiments, to determine an output based on such 3D invariant images, the image processing unit 115 can thereby disregard at least some differences in imaging parameters in the acquisition and/or post-processing of the 3D anatomical images, and only focus on the structurally relevant isophote structure of the 3D anatomical images for the analysis purposes.

In some embodiments, the isophote structure invariant entity is a mean curvature of isophotes. Such mean curvature of isophotes can be computed based on an equation equivalent to the following equation:

$$\kappa = div\left(\frac{\nabla I}{\|\nabla I\|}\right), \quad (1)$$

where $\kappa$ represents the mean curvature of isophotes, I represents the image, div (*) denotes the divergence of *, $\nabla$* denotes the gradient of *, and $\|*\|$ denotes the absolute value of *.

Figure 3B:
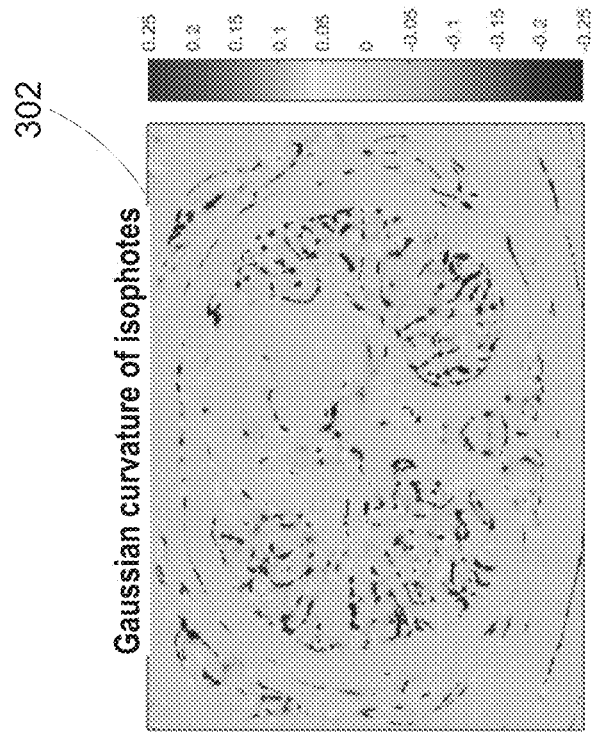
FIG. 3B is an example of a 3D invariant image section generated by processing the 3D anatomical image section of FIG. 2A based on a Gaussian curvature of isophotes, in accordance with one or more embodiments.
Figure 3A:
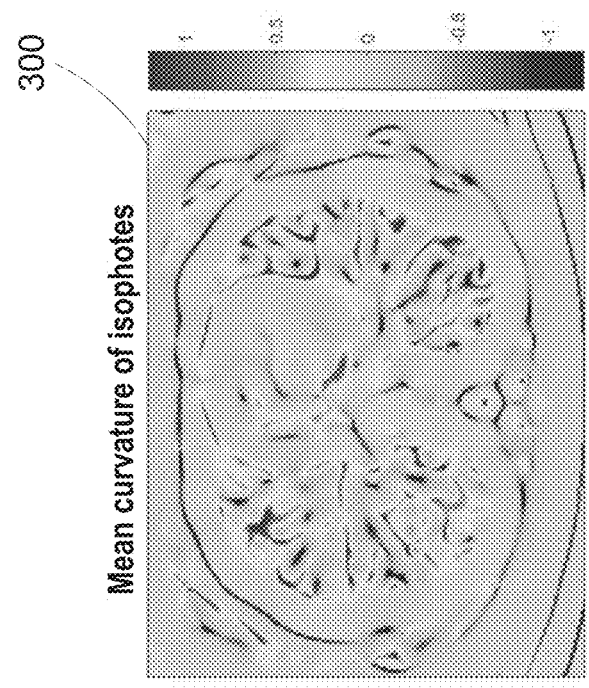
FIG. 3A is an example of a 3D invariant image section generated by processing the 3D anatomical image section of FIG. 2A based on a mean curvature of isophotes, in accordance with one or more embodiments.

FIG. 3A shows a 3D invariant image section 300 resulting from the processing of the 3D anatomical image section 200 of FIG. 2A on the basis of a mean curvature of isophotes.

Many other equivalent formulations of the mean curvature of isophotes exist. For instance, the mean curvature of isophotes can also be written explicitly in terms of image derivatives such as shown in the following equation:

$$\kappa = \frac{\begin{bmatrix} I_x^2(I_{yy} + I_{zz}) - 2I_y I_z I_{yz} + \\ I_y^2(I_{xx} + I_{zz}) - 2I_x I_z I_{xz} + \\ I_z^2(I_{xx} + I_{yy}) - 2I_x I_y I_{xy} \end{bmatrix}}{(I_x^2 + I_y^2 + I_z^2)3/2}. \quad (2)$$

It is noted that the denominator of equation (2) can be multiplied by a factor 2, as this can denote a constant scaling factor. Presence or absence of such constant scaling factor is irrelevant to the generation of the 3D invariant image(s) on the basis of this isophote structure invariant entity.

In some embodiments, the isophote structure invariant entity is a Gaussian curvature of isophotes. Such Gaussian curvature of isophotes can be computed based on an equation equivalent to:

$$H = \frac{\begin{bmatrix} I_x^2(I_{yy}I_{zz} - I_{yz}^2) + 2I_yI_z(I_{xz}I_{xy} - I_{xx}I_{yz}) + \\ I_y^2(I_{xx}I_{zz} - I_{xz}^2) + 2I_xI_z(I_{yz}I_{xy} - I_{yy}I_{xz}) + \\ I_z^2(I_{xx}I_{yy} - I_{xy}^2) + 2I_xI_y(I_{xz}I_{yz} - I_{zz}I_{xy}) \end{bmatrix}}{(I_x^2 + I_y^2 + I_z^2)^2}, \quad (3)$$

wherein H denotes the Gaussian curvature of isophotes. The Gaussian curvature of isophotes involves explicit image derivatives such as expressed in equation (3).

FIG. 3B shows a 3D invariant image section 302 resulting from the processing of the 3D anatomical image section 200 of FIG. 2A on the basis of a Gaussian curvature of isophotes. As can be appreciated, the 3D invariant image sections 300 and 302 are different from one another, and they can thus be both used by the image processing unit 115 to determine a desired output. In some embodiments, feeding a greater number of different 3D invariant images to the image processing unit 115 can result in generating the output faster and/or generating an output which is more accurate and/or reliable.

The mean curvature of isophotes and the Gaussian curvature of isophotes described above are only meant to be examples of the isophote structure invariant entity with which the 3D anatomical images can be processed. Indeed, other isophote structure invariant entities exist as well. However, in some embodiments, these other isophote structure invariant entities can involve higher-order derivatives which may be less stable to compute.

The mean curvature of isophotes and the Gaussian curvature of isophotes can also be defined in terms of principal curvatures of the isophotes, as per the following equations:

$$\kappa = \frac{k_1 + k_2}{2}, \text{ and} \quad (4)$$

$$H = k_1 k_2, \quad (5)$$

wherein $k_1$ and $k_2$ are the two principal curvatures of isophote, which are also isophote structure invariant entities. Specifying the mean curvature of isophote and the Gaussian curvature of isophote can define the two principal curvatures of isophote, and conversely, specifying the two principal curvatures of isophotes can define the mean curvature of isophote and the Gaussian curvature of isophote.

Figure 4:
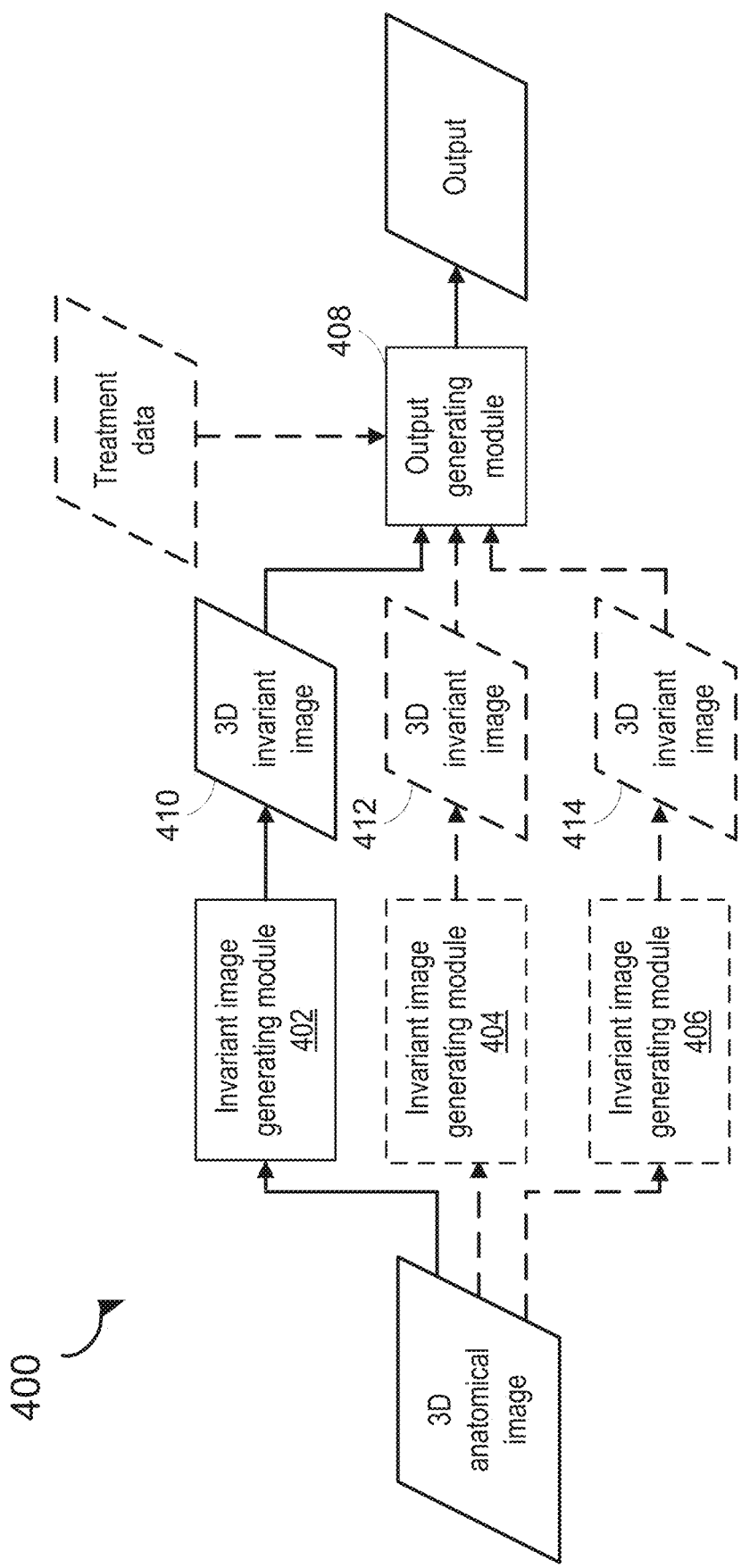
FIG. 4 is a schematic view of an example of a software application of the system of FIG. 1, in accordance with one or more embodiments.

Referring now to FIG. 4, there is shown an example of a software application 400 implementing the method(s) described herein. As shown, software application 400 has invariant image generating module(s) 402, 404 and 406 image and an output generating module 408.

As shown, the invariant image generating module 402 receives a 3D anatomical image representing a region of a body of a patient. Upon processing the 3D anatomical image based on a first isophote structure invariant entity, a first 3D invariant image 410 is generated. The first 3D invariant image 410 can thus be transmitted to the output generating module 408 which processes the first 3D invariant image 410 and generates an output based on the processing of the first 3D anatomical image 410.

In some embodiments, the output generating module 408 receives treatment data representative of treatment received by the patient. In these embodiments, the processing upon which is based the generation of the output can be further based on the treatment data so as to generate medical treatment outcome data indicative of an outcome assessment of a treatment received by said patient. For instance, the medical treatment outcome data can be provided in the form of a likelihood of success of the treatment.

As shown in this example, the software application 400 has invariant image generating modules 404 and 406 which are each configured to receive the 3D anatomical image and to process the 3D anatomical image based on second and third isophote structure invariant entities to generate respective invariant images 412 and 414. As it can be appreciated, the first, second and third isophote structure invariant entities are different from one another and accordingly the first, second and third invariant images 410, 412 and 414 are different from one another. In this embodiment, the output can be generated upon processing not only the first invariant image 410 but all of the first, second and third invariant images 410, 412 and 414. Although the embodiment illustrated in FIG. 4 shows that three isophote structure invariant entities are used, the number of different isophote structure invariant entities can differ in some other embodiments. For instance, the invariant image generating module 406 can be omitted in some embodiments, thereby leaving only the first and second invariant image modules 402 and 404. In these embodiments, the first invariant image generating module 402 can involve the mean curvature of isophotes whereas the second invariant image generating module 404 can involve the Gaussian curvature of isophotes.

The invariant images 410, 412 and 414 can thereby be as input to the output generating module 408 which may include a statistical analysis unit and/or a machine learning unit, either alone or in conjunction with each other, in order to achieve a prediction of response to treatment, a prediction of outcome, a condition diagnosis, a cancer stage classification, and/or any other desirable output as may be required of system 100.

Referring back to system 100 can be software (e.g., code segments compiled into machine code), hardware, embedded firmware, or a combination of software and hardware, according to various embodiments.

System 100 is configured to receive one or more data sets representative of one or more 3D anatomical images (hereinafter referred to simply as "3D anatomical images") from a medical imaging system 130 through network 150. System 100 can receive or access the one or more 3D anatomical images through an image acquisition unit 111 stored on memory 109.

A processor or processing device 101 can execute instructions in memory 109 to configure various components or units 111, 113, 115, 117. A processing device 101 can be, for example, any type of general-purpose microprocessor or microcontroller, a digital signal processing (DSP) processor, an integrated circuit, a field programmable gate array (FPGA), a reconfigurable processor, or any combination thereof.

Each communication interface 105 enables the system 100 to communicate with other components, to exchange data with other components, to access and connect to network resources, to serve applications, and perform other computing applications by connecting to a network (or multiple networks) capable of carrying data including the Internet, Ethernet, plain old telephone service (POTS) line, public switch telephone network (PSTN), integrated services digital network (ISDN), digital subscriber line (DSL), coaxial cable, fiber optics, satellite, mobile, wireless (e.g. W-Fi, WiMAX), SS7 signaling network, fixed line, local area network, wide area network, and others, including any combination of these.

Each I/O unit 107 enables the system 100 to interconnect with one or more input devices, such as a keyboard, mouse, camera, touch screen, a microphone and the like, or with one or more output devices such as a display screen, a speaker, a printer and the like.

Memory 109 may include a suitable combination of computer memory such as, for example, static random-access memory (SRAM), random-access memory (RAM), read-only memory (ROM), electro-optical memory, magneto-optical memory, erasable programmable read-only memory (EPROM), and electrically-erasable programmable read-only memory (EEPROM), Ferroelectric RAM (FRAM) or the like.

Data storage 110 can be, for example, one or more NAND flash memory modules of suitable capacity, or may be one or more persistent computer storage devices, such as a hard disk drive, a solid state drive, and the like.

An image acquisition unit 111 may be configured to acquire or receive one or more 3D anatomical images. The 3D anatomical images may be represented by one or more data sets. In some embodiments, a 3D anatomical image in digital form may include arrays of pixels, and each pixel may be represented by one or more channels (or components) of data. The data sets may be single-channel or multi-channel. For example, a grey-scale 3D anatomical image may have just one channel whereas a color image may include a red (R) channel, a green (G) channel and a blue (B) channel. Image acquisition unit 111 can store the acquired 3D anatomical 3D anatomical images in data storage 110.

In some embodiments, image acquisition unit 111 is communicatively coupled to medical imaging system 130 and receives instructions therefrom, for example to acquire and/or generate the 3D anatomical images. Image acquisition unit 111 may be further configured for sending the 3D anatomical images to data storage 180 or to other units of system 100.

3D anatomical images in some embodiments may contain a single numerical value at each pixel, typically referred to as "intensity." However, some 3D anatomical images may have more than a single value at each pixel. Such 3D anatomical images are known as multi-channel images. One multi-channel image example is a RGB color image, where each pixel contains three values used to encode color. These three values are referred to as "channels." The same procedure described above for processing the 3D anatomical images based on one or more isophote structure invariant properties can be applied individually to each channel of such multi-channel images. This can be achieved, for instance, by first splitting one multi-channel image into several single-channel image. Alternatively, the channels of the multi-channel image can be combined together to produce a single valued image, which can then be used as input to the procedure described above. Yet another option is to define gradient operations directly on multi-channel images, in order to compute a higher-order equivalent of curvature.

An image pre-processing unit 113 may be configured to pre-process the 3D anatomical images. Since image-processing (e.g., curvature computations) can be sensitive to noise, a smoothing operation such as Gaussian filtering may be performed on the 3D anatomical image to remove noise, for instance noise related to voxel discretization or to image acquisition parameters. Such filtering can also serve to enhance structures of a particular spatial scale in the image. Such a smoothing operation can be performed in many different ways. An example approach may be to perform a convolution of the 3D anatomical image with a Gaussian filter of a pre-defined standard deviation. This may be an optional step performed by an example system prior to processing a 3D anatomical image.

In some embodiments, image pre-processing unit 113 may convert a color image into a greyscale image, as configured by a default setting or by a user.

An image processing unit 115 may be configured to process the 3D anatomical images from data storage 110. For example, in some embodiments, image processing unit 115 may be configured to process the 3D anatomical images to compute the isophote structure invariant entity as described herein. For example, image processing unit 115 may be configured to retrieve one or more data sets representing a 3D anatomical image, and compute one or more data sets representing a isophote structure invariant entity for the 3D anatomical image.

In an N-dimensional image, with $N \geq 3$, an isophote is defined as a (N−1) dimensional manifold, such that its points have equal image values (e.g., equal brightness or luminance).

The term "curvature" refers to the notion of deviation from flatness. In mathematics, there are several different ways of defining this notion, depending on the specific context. For instance, in the case of a smooth curve on the 2D plane, the curvature at a point is defined relative to the rate of change of the curve's tangent vector at that point. Alternatively, the curvature at a point along the curve can also be defined as the inverse of the radius of the circle that approximates the curve the most tightly at that point (the osculating circle). In the case of curves, surfaces and other geometrical objects in three and higher dimensions, their curvature is described in more complex ways. For instance, one of the most general way of defining curvature is via the Riemann curvature tensor.

In the specific case of surfaces embedded in 3D space, as is the case of isophotes in 3D medical imaging, a "mean curvature" may be used. One of the definitions for mean curvature of a surface in 3D is the divergence of the unit normal vector field. Given that isophotes in 3D anatomical images can be implicitly defined as the surfaces that are locally orthogonal to the image intensity gradient, it follows that the isophote mean curvature corresponds to the divergence of the unit intensity gradient of the image such as shown in equation (1) above. In this equation, $\kappa$ denotes the mean curvature, and I represents the image. Other equivalent definitions can be used. For instance, mean curvature can alternatively be defined based on the trace of the Hessian matrix, or based on the first and second derivatives of the image, as defined in equation (2) above. Regardless of the particular definition used, however, the isophote curvature at a given point in the image is computed via local information only, i.e., using only information from the local image neighborhood, which may include an abnormality such as a tumor core and the immediate surrounding region of the tumor core.

In some embodiments, the mean curvature definition given in equation (1) is utilized by an example system for performing medical treatment outcome assessment or medical condition diagnostic, though other formulations of curvature may be used as well. Other such measures of curvature include, for instance, the above-described Gaussian curvature of isophotes, or measures derived from the Riemann curvature tensor. Furthermore, in some embodiments, the mean curvature of the isophotes may be a scalar number computed at each pixel/voxel of the image. In other embodiments, curvature information can also be represented by a higher dimensional object, such as a vector or a tensor.

As experimental results described below demonstrate, information regarding isophote structure invariant entities in 3D anatomical images may be correlated with success of cancer treatment in one or more patients. That is, a certain change in curvature of isophotes in 3D anatomical images of a tumor (and its surrounding regions) may be correlated to a higher likelihood of success of a cancer treatment given to a patient. Therefore, based on the information comprised in invariant images of at least two 3D anatomical images, a prediction may be generated for a likelihood of success of a cancer treatment to Patient A, if the two 3D anatomical images demonstrate a change of curvature of isophotes identical or sufficiently similar to a change previously correlated to a positive or negative progress of Patient B's condition after the cancer treatment has been given to Patient B.

A machine learning unit 117 may be configured to process one or more data sets representative of 3D invariant images of one or more 3D anatomical images and generate an output comprising a diagnosis, or prediction regarding a likelihood of success for a cancer treatment, or for any other type of condition, such as chronic disease.

In some embodiments, machine learning techniques may be used to generate a prediction regarding a likelihood of success for a cancer treatment, or for any other type of condition, based on the 3D invariant images computed from the 3D anatomical images based on one or more isophote structure invariant entity. For example, features extracted using isophotes and curvatures imaging analysis may be analyzed using machine learning to build models for predicting a diagnosis, or a likelihood of success for a cancer treatment or treatment for other types of condition, such as chronic disease.

A training unit (not illustrated) may be configured to process one or more data sets representative of 3D anatomical images and/or 3D invariant images as defined above for training one or more models for generating predictions regarding diagnosis, or likelihood of success by one or more treatments. In some embodiments, the training may be unsupervised. In some other embodiments, the training may be supervised.

One or more machine learning modes may be stored in data storage, rankings of filters and weights, and associated rules, may be stored in data storage 110, which is configured to maintain one or more data sets, including data structures storing linkages. Data storage 110 may be a relational database, a flat data storage, a non-relational database, among others. System 100 may be configured to implement one or more components or units for training and improving machine learning model(s) over time.

In some embodiments, system 100 may include a user interface unit (not illustrated) configured for providing or facilitating an interface, such as a user interface, to connect to external databases and systems. The interface may allow one or more administrators and users to configure the settings of system 100, such as for example, medical imaging parameters.

Figure 5:
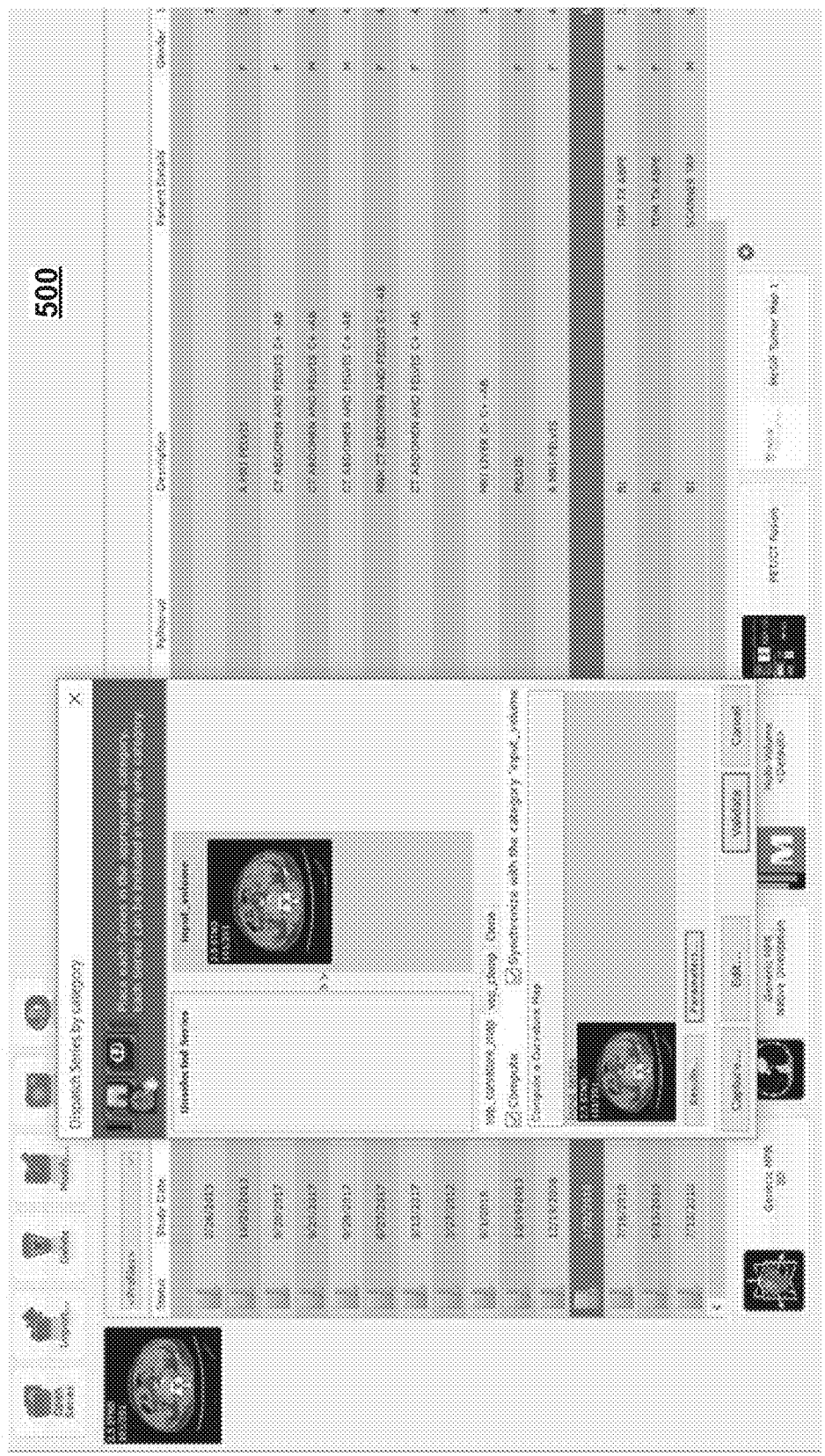
FIG. 5 is an example screen shot of an example system for performing medical treatment outcome assessment or medical condition diagnostic, in accordance with one or more embodiments.

Referring to FIG. 5, which an example screen shot 300 of a user interface of system 100 for performing medical treatment outcome assessment or medical condition diagnostic, according to some embodiments. As shown, system 100 may allow a user to select a medical study, which may include one or more 3D anatomical images, for processing. The user may accept default settings or modify one or more parameter values associated with the image processing.

Figure 6:
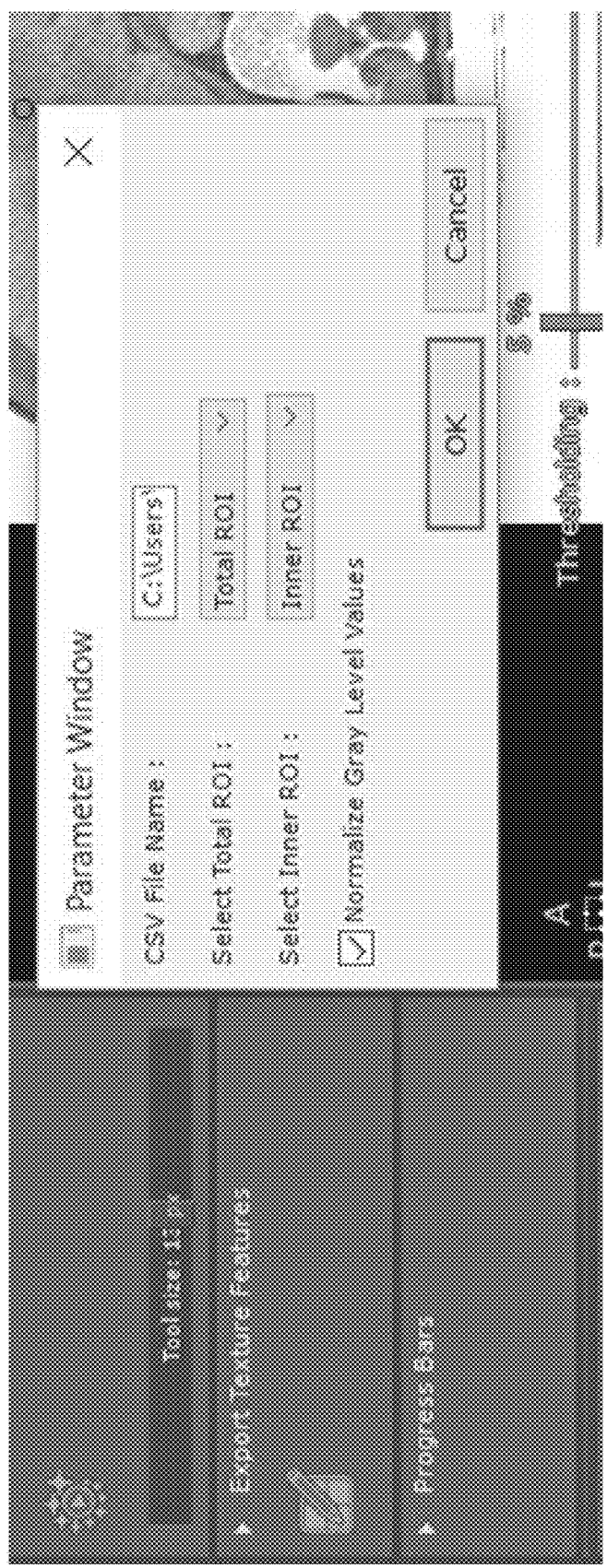
FIG. 6 is another example screen shot of an example system for performing medical treatment outcome assessment or medical condition diagnostic, in accordance with one or more embodiments.

FIG. 6 is another example screen shot of a user interface of system 100 for performing medical treatment outcome assessment or medical condition diagnostic displaying a parameter window, according to some embodiments. A user may select different region-of-interest (ROI) for processing a 3D anatomical image. For example, a user may select a Total ROI representing the tumor's inner core and a region surrounding the tumor (also known as a "border region"), an Inner ROI representing just the tumor in the 3D anatomical image, or only a ROI of the border region, which describes the periphery of the inner tumor portion. A user may also choose to normalize gray level values of a 3D anatomical image.

Figure 7:
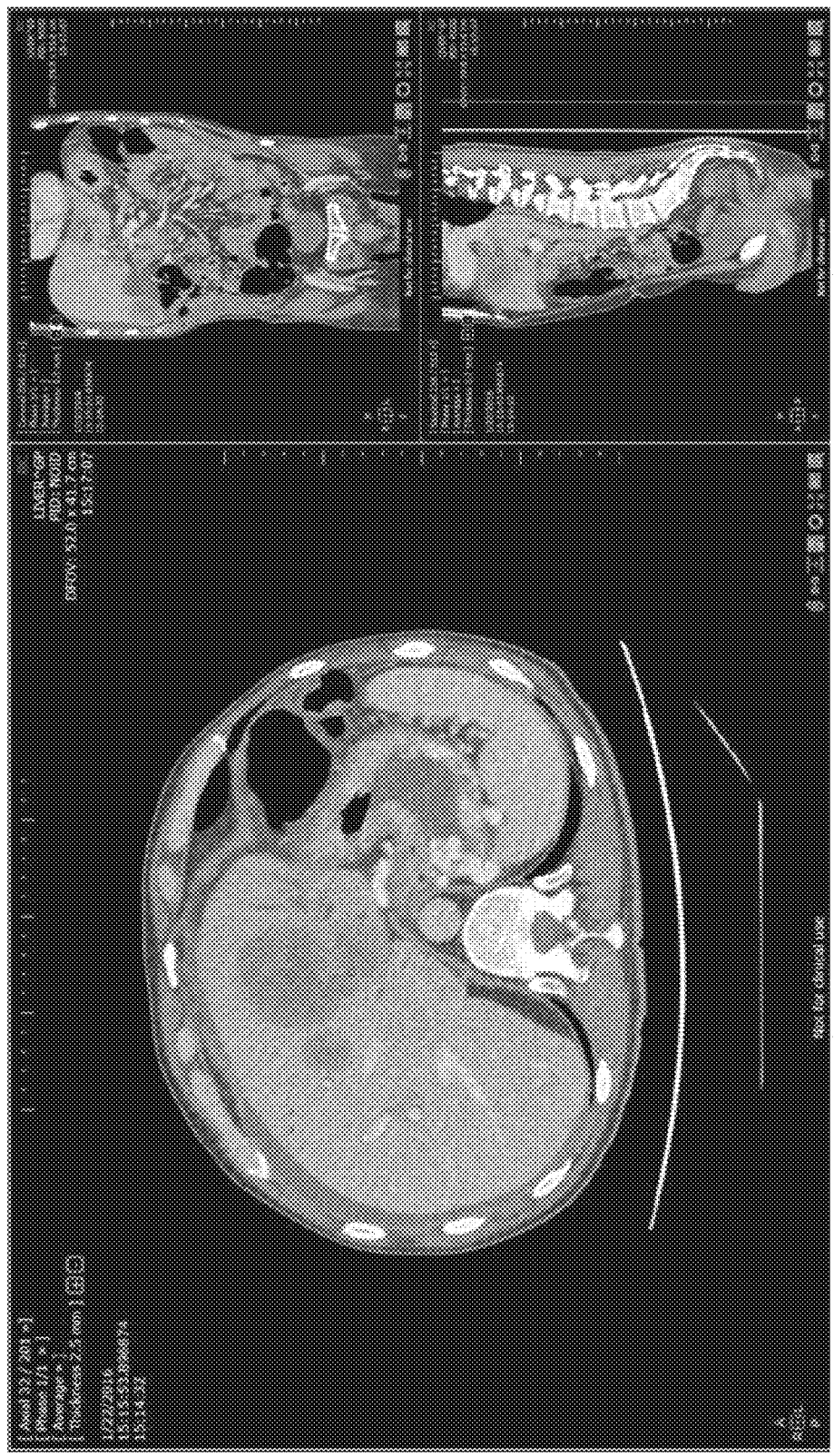
FIG. 7 shows example 3D anatomical image sections displayed by an example system for performing medical treatment outcome assessment or medical condition diagnostic, in accordance with one or more embodiments.

In some embodiments, system 100 may be configured to display a 3D anatomical image in one or more planner sections, as shown in FIG. 7. System 100 can show multi-planar visualization of 3D images, such as a top view, a side view, and a bottom view of a 3D anatomical image of an abdominal scan of a patient.

Figure 8:
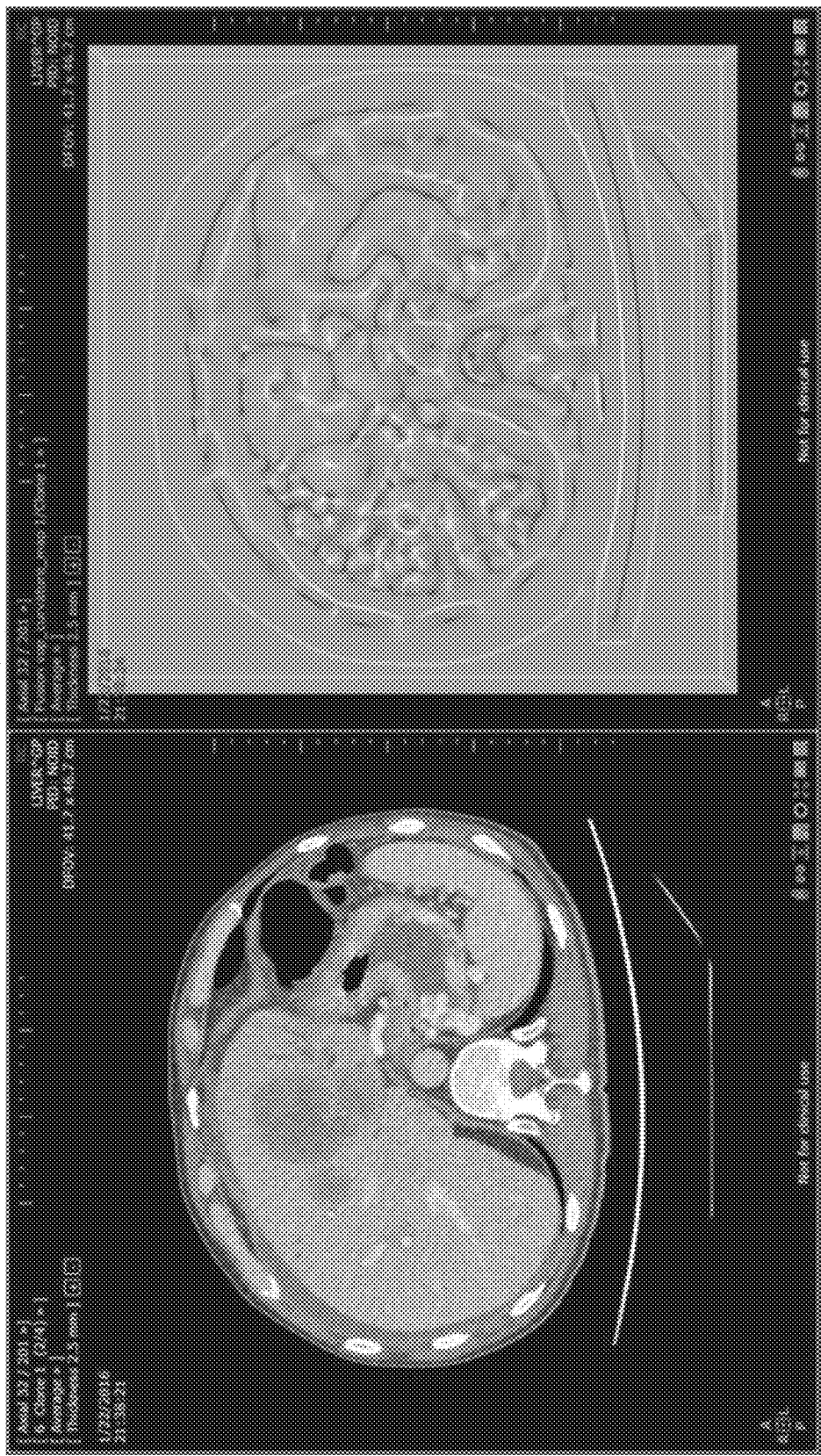
FIG. 8 shows an example 3D anatomical image section of an abdomen scan with measurements of curvature of isophotes displayed by an example system for performing medical treatment outcome assessment or medical condition diagnostic, in accordance with one or more embodiments.

In some embodiment, once the 3D anatomical image is processed, system 100 may be configured to display the 3D anatomical image along, any generated invariant images and/or a graphical representation of the curvature of isophotes, once the invariant image and/or the curvature of isophotes have been computed by image processing unit 115. For example, the graphical representation may be displayed alongside the 3D anatomical image, as shown in FIG. 8, where the a section view of the abdomen scan is shown on the left hand side, and a corresponding view of the abdomen scan with graphical representation of the curvature of isophotes is shown on the right hand side.

Figure 9:
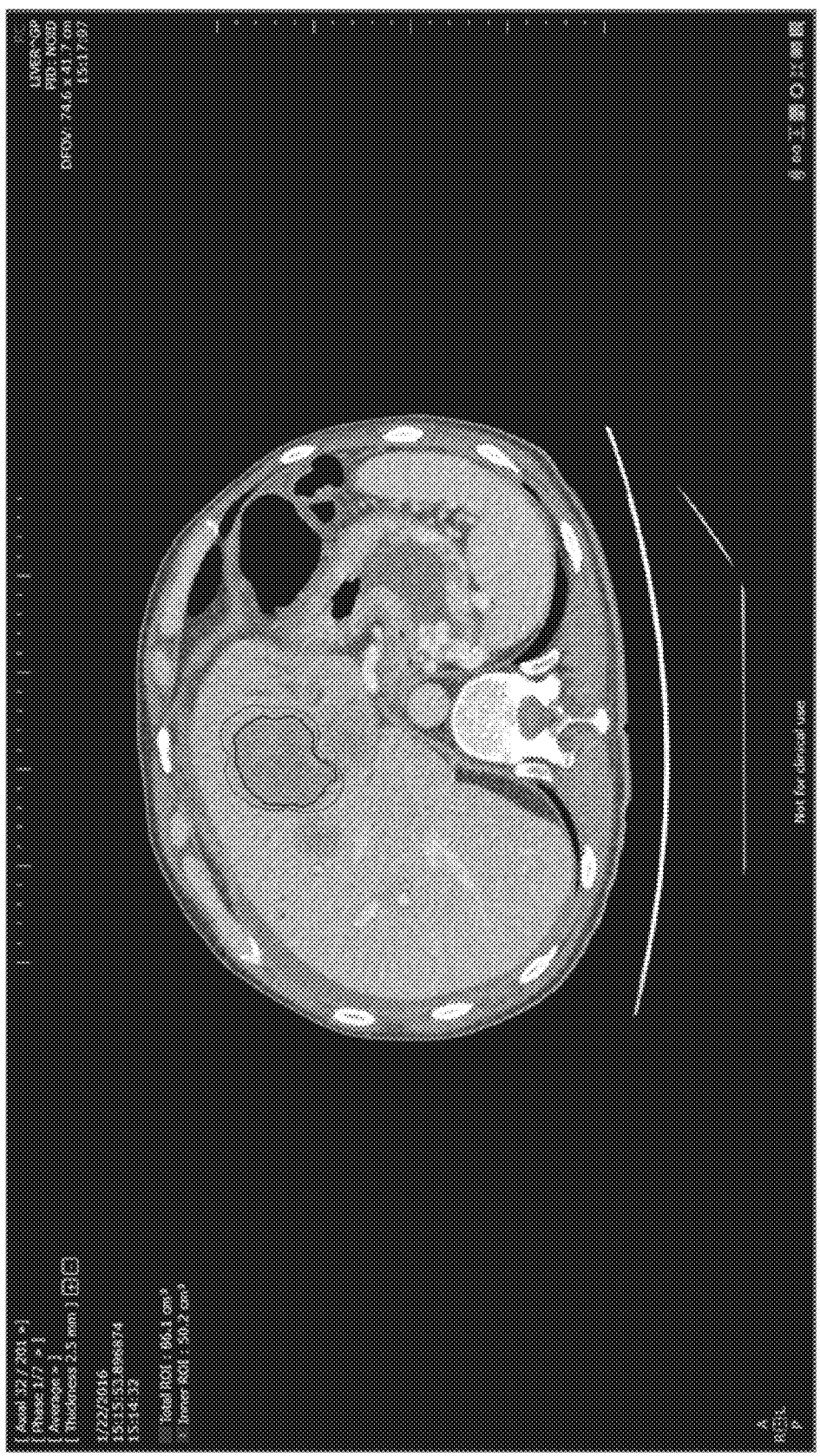
FIG. 9 shows an example 3D anatomical image section of an abdomen scan with a segmentation of a tumor in the liver, displayed by an example system for performing medical treatment outcome assessment or medical condition diagnostic, in accordance with one or more embodiments.
Figure 10:
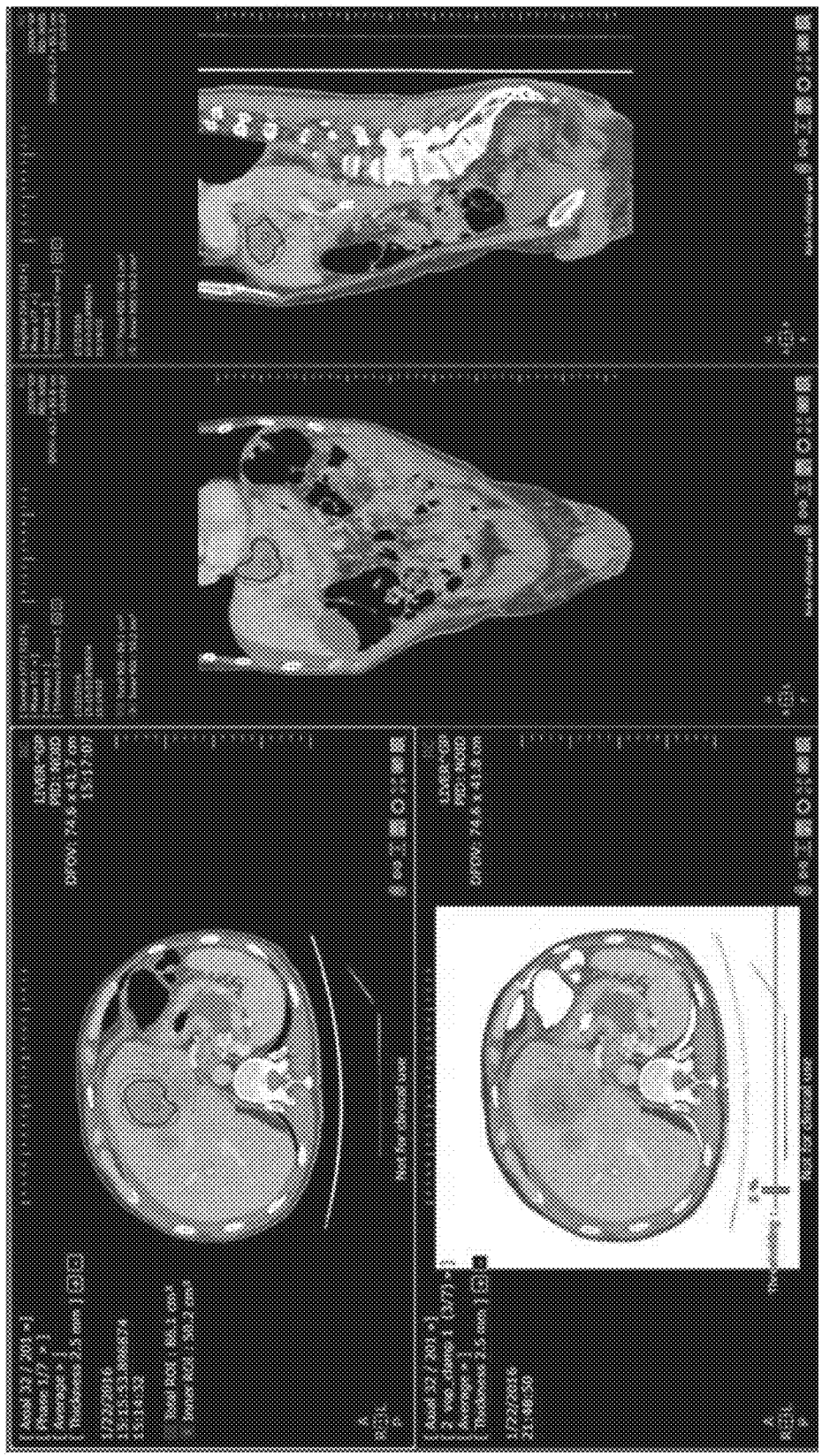
FIG. 10 shows different planar views of a 3D anatomical image section of an abdomen scan with a segmentation of a tumor in the liver, displayed by an example system for performing medical treatment outcome assessment or medical condition diagnostic, in accordance with one or more embodiments.

In some embodiments, system 100 may be configured to display and process segments or portions of a 3D anatomical image. For example, system 100 may be configured to detect a region in the 3D anatomical image containing an abnormality such as a tumor and proceed to examine the region containing the tumor, such that the region containing the tumor as well as its immediate surrounding region (e.g., the periphery region around the tumor core) can be automatically processed and displayed, as shown in FIGS. 9 and 10. FIG. 9 shows an example 3D anatomical image of an abdomen scan with a liver tumor segmentation displayed by system 100. FIG. 10 shows different planar views of the 3D anatomical image of the abdomen scan with a liver tumor segmentation, as displayed by system 100.

In some embodiments, system 100 may be configured to automatically select and process the region of a 3D anatomical image containing the tumor and its immediate surrounding region (collectively "total ROI") to compute the curvature of isophotes information regarding the selected region. In some embodiments, instead of the total ROI, a segmentation of the tumor core represented by an Inner ROI in a 3D anatomical image may be processed by system 100.

Figure 11:
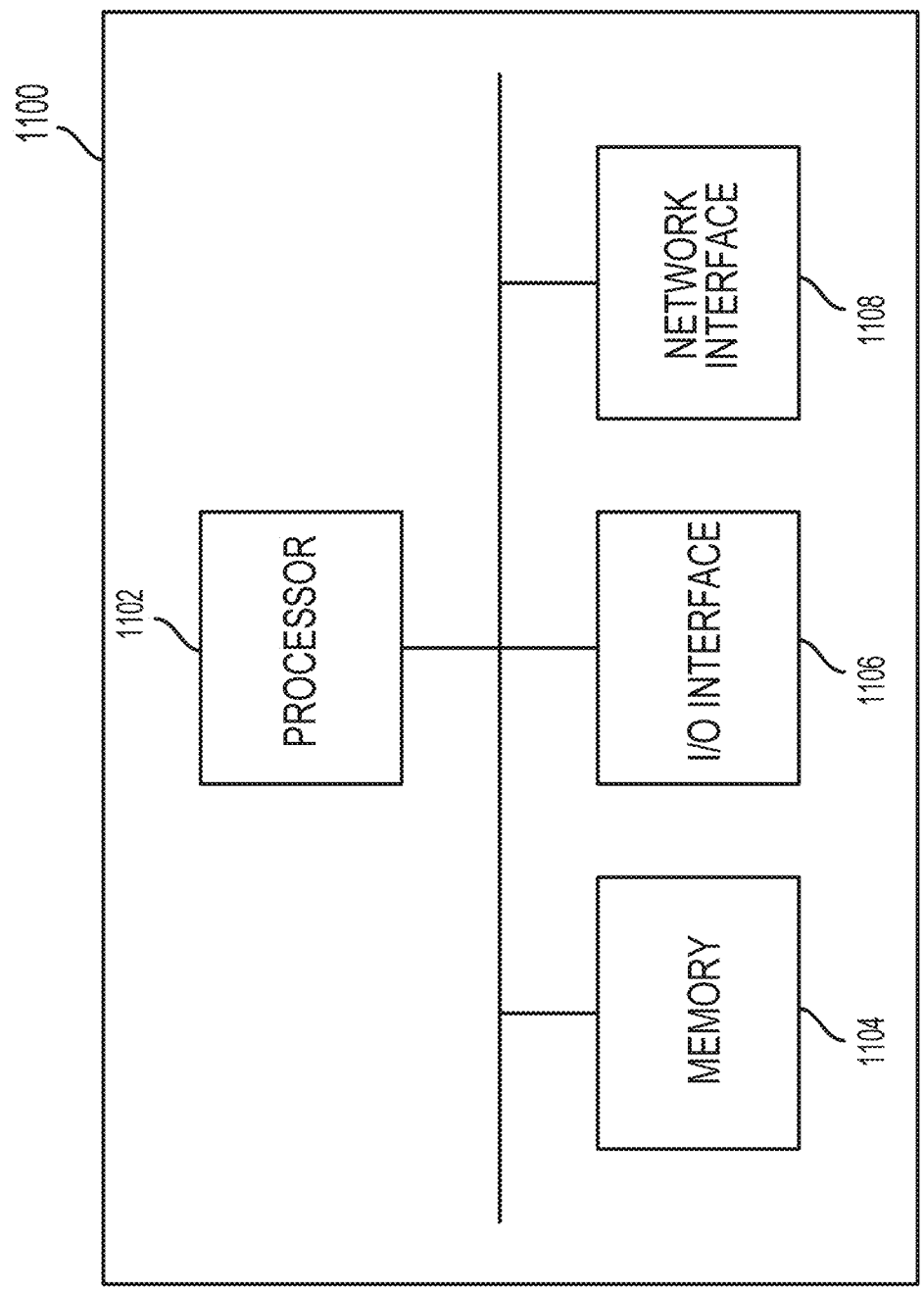
FIG. 11 is an example block diagram of an example computing device, in accordance with one or more embodiments.

FIG. 11 is a schematic block diagram of an example computing device 1100 implementing system 100, according to some embodiments. As depicted, computing device 1100 includes at least one processor 1102, memory 1104, at least one I/O interface 1106, and at least one network interface 1108. The computing device 1100 may be configured as a machine learning server adapted to dynamically maintain one or more neural networks.

Each processor 1102 may be a microprocessor or microcontroller, a digital signal processing (DSP) processor, an integrated circuit, a field programmable gate array (FPGA), a reconfigurable processor, a programmable read-only memory (PROM), or combinations thereof.

Memory 1104 may include a computer memory that is located either internally or externally such as, for example, random-access memory (RAM), read-only memory (ROM), compact disc read-only memory (CDROM), electro-optical memory, magneto-optical memory, erasable programmable read-only memory (EPROM), and electrically-erasable programmable read-only memory (EEPROM), Ferroelectric RAM (FRAM).

Each I/O interface 1106 enables computing device 1100 to interconnect with one or more input devices, such as a keyboard, mouse, camera, touch screen and a microphone, or with one or more output devices such as a display screen and a speaker.

A networking interface 1108 may be configured to receive and transmit data sets representative of the machine learning models, for example, to a target data storage or data structures. The target data storage or data structure may, in some embodiments, reside on a computing device or system such as a mobile device.

Figure 12:
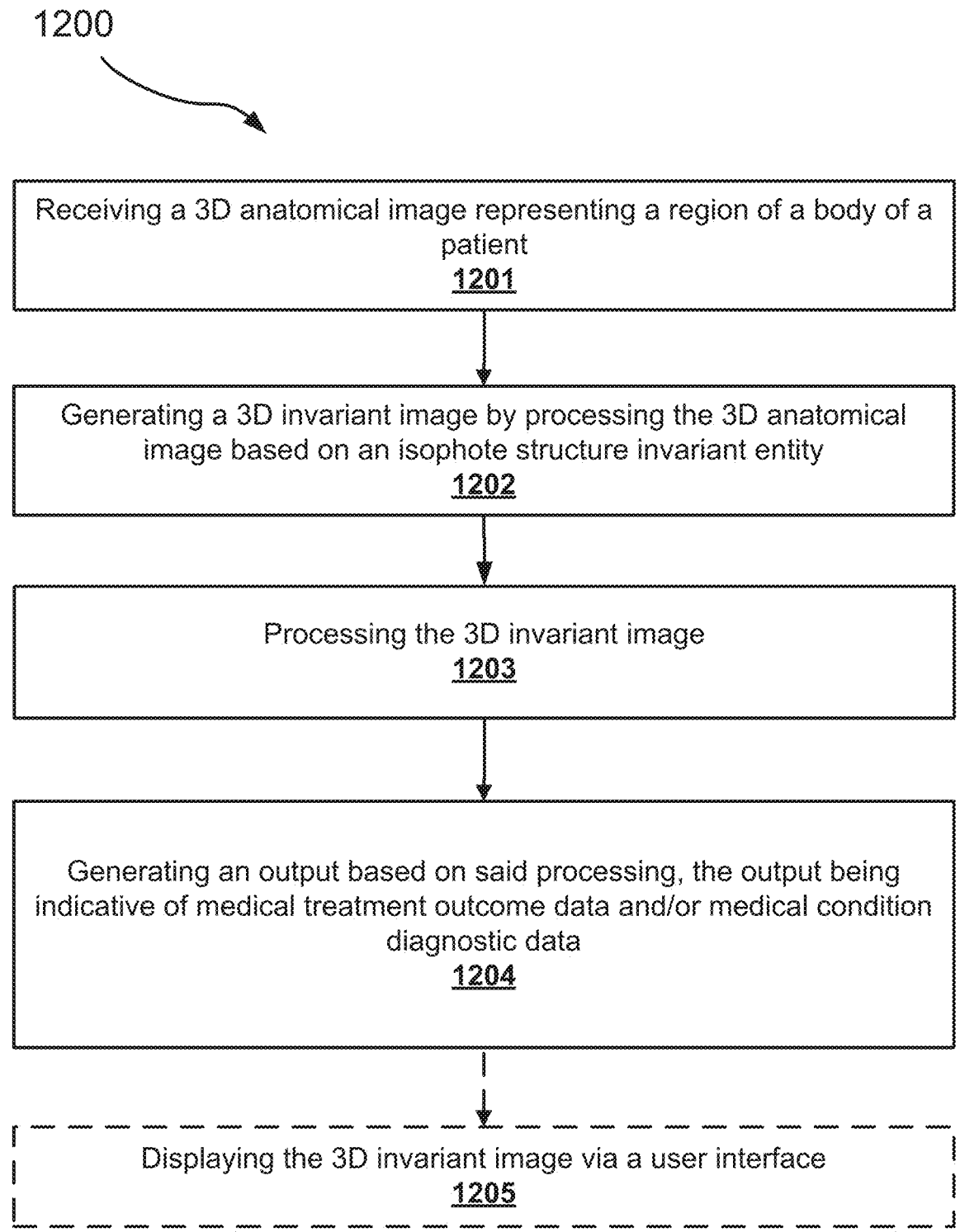
FIG. 12 is an example flow chart representing a method performed by a system for performing medical treatment outcome assessment or medical condition diagnostic, in accordance with one or more embodiments

Referring now to FIG. 12, which illustrates an example flow chart representing a method 1200 performed by system 100 for performing medical treatment outcome assessment or medical condition diagnostic, according to some embodiments.

At step 1201, system 100 may be configured to receive a 3D anatomical image representing a region of a body of a patient.

At step 1202, system 100 may be configured to generate a 3D invariant image by processing the 3D anatomical image based on an isophote structure invariant entity.

At step 1203, system 100 may be configured to process the 3D invariant image.

At 1204, system 100 may be configured to generate an output based on the processing performed at step 1203. The output being either medical treatment outcome data indicative of an outcome assessment of a treatment received by said patient, or medical condition diagnostic data indicative of a diagnostic of a medical condition of said patient.

EXPERIMENTAL RESULTS

Experiment 1: Response Prediction on Liver Tumors in CT Imaging

An experiment has been conducted based on 3D anatomical images taken before and after treatment in thirty cancer patients who had liver tumors. Out of these thirty (30) patients, fifteen (15) patients had a positive treatment response, and fifteen (15) patients had a negative treatment response. The patients were part of a research clinical trial and the clinical outcome (positive and negative responses) were validated. For each patient, 3D anatomical images were taken and processed based on isophote structure invariant entity (e.g., curvature of isophotes) to generate invariant images or equivalent respective data sets. The data sets were then averaged over the spatial extent of the largest tumor in the liver, before and after the cancer treatment. The 3D anatomical images were taken at two points in time: baseline image(s) were taken before the cancer treatment, and follow-up images were taken two months after the cancer treatment.

Specifically, system 100 performed a tumor segmentation on the baseline images and the follow-up images. The tumor segmentation refers to a segmentation of the largest tumor in the medical image. The following statistics were computed over the segmented region of the medical images in regards to both curvature of isophotes and native intensity: (1) mean, (2) standard deviation, (3) skewness, (4) kurtosis, and (5) entropy.

Figure 13A:
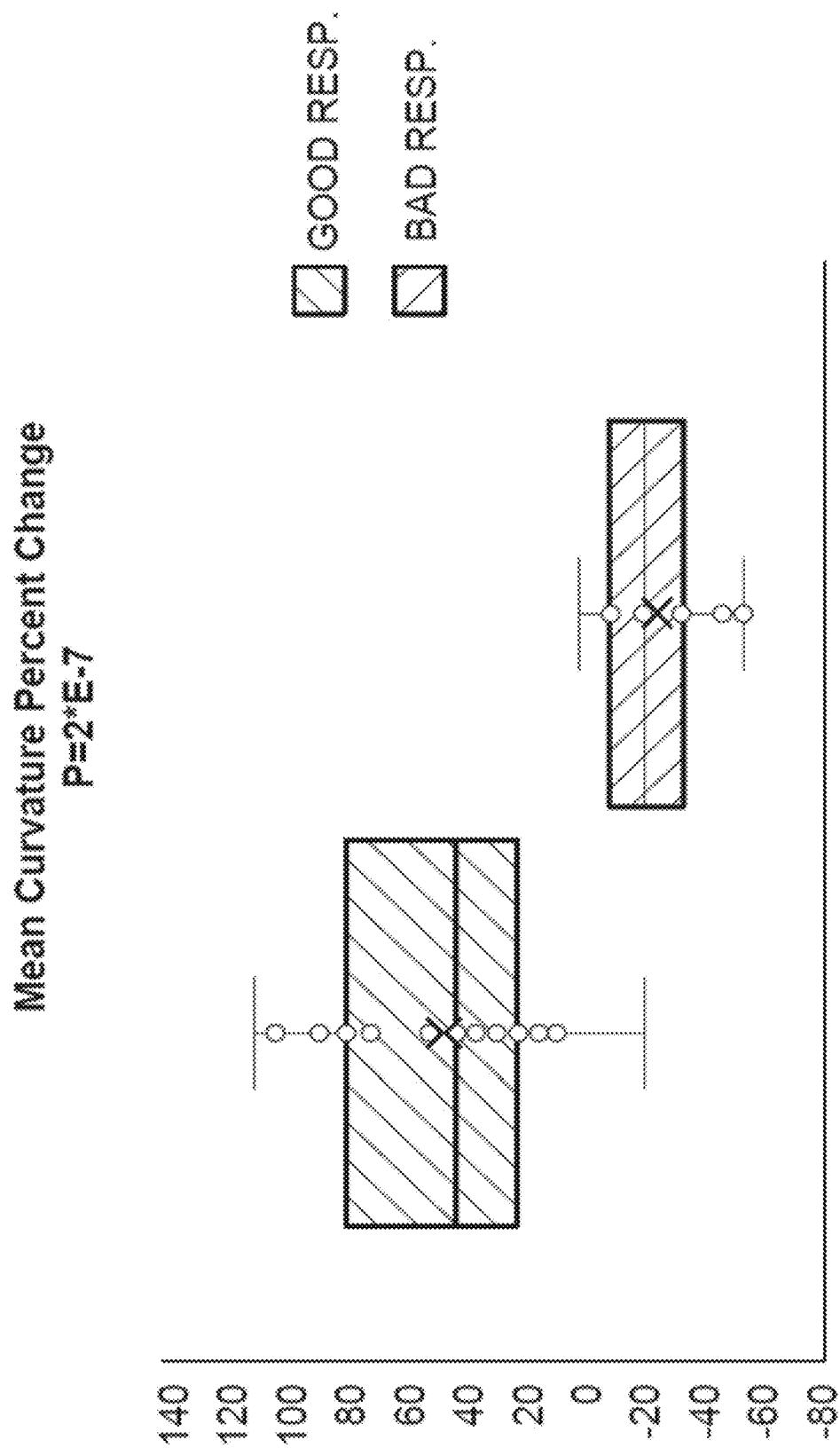
FIG. 13A is a graph showing a percentage change of mean curvature of isophotes based on 3D anatomical images taken during a period of two months, in accordance with one or more embodiments.

FIG. 13A is a graph showing a percentage change of mean curvature of isophotes based on medical images taken during a period of two months. This may be referred to as a change in the mean value of curvature map.

Figure 13B:
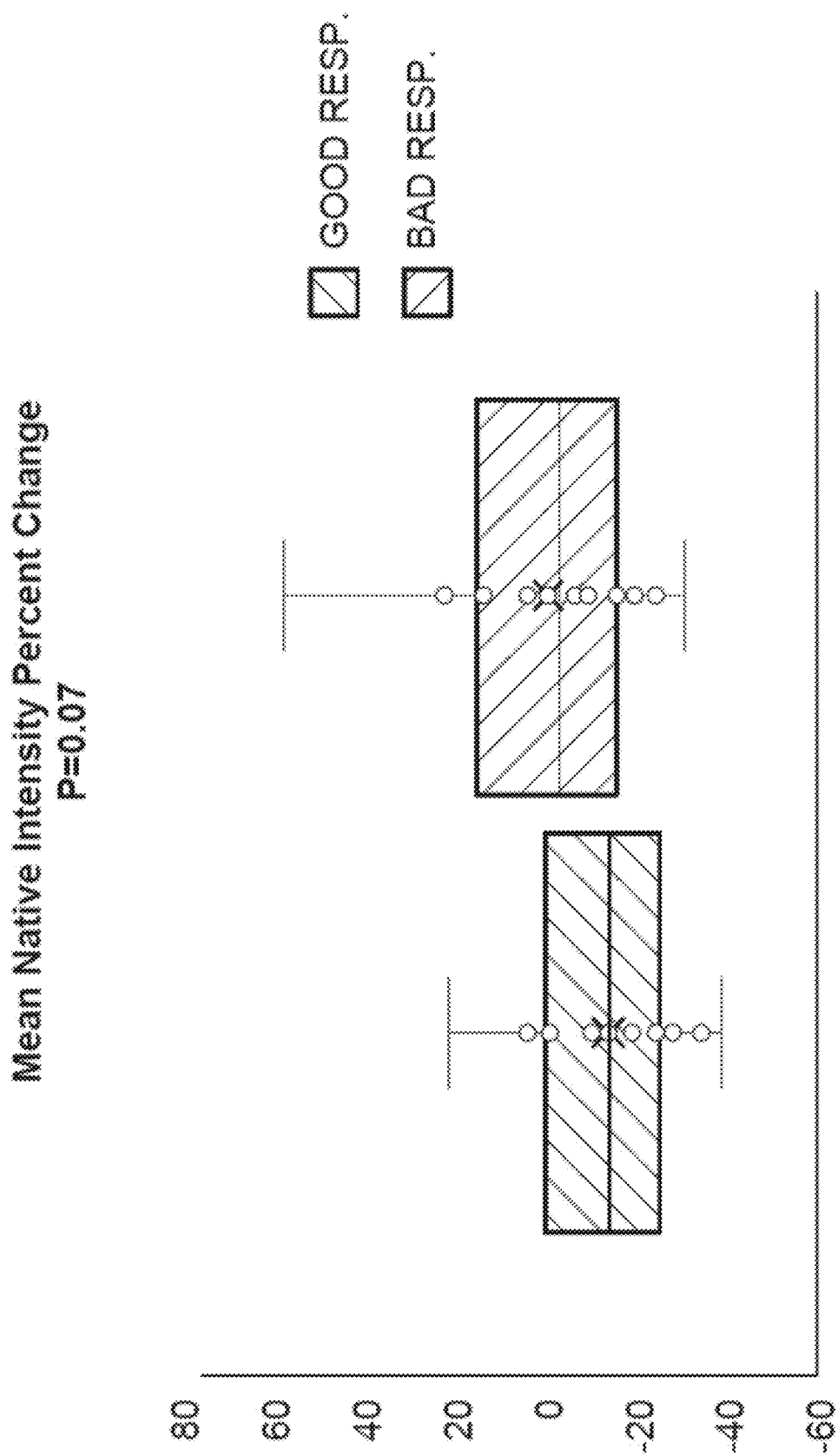
FIG. 13B is a graph showing a percentage change of native intensity based on 3D anatomical images taken during a period of two months, in accordance with one or more embodiments

FIG. 13B is a graph showing a percentage change of mean native intensity based on medical images taken during a period of two months.

When looking at the change in the mean value of curvature map, between baseline images and the 2-month follow-up images, a very strong separation between the positive and negative responses may be observed at baseline (i.e., $p=2*10e-7$ in FIG. 8A), which is not seen when examining the native intensity images ($p>0.05$ in FIG. 13B).

These results indicate that the curvature of isophotes may, in some embodiments, be used to predict positive or negative response of a cancer treatment for a patient, as soon as two months post-treatment.

Experiment 2: Quantitative Image Analysis on Growth Patterns of Liver Metastases from Colorectal Cancer: Preliminary Results The purpose of this experiment was to assess the ability of delayed post contrast MRI and quantitative image analysis to predict histopathological growth patterns (HGP) of colorectal cancer liver metastases (CRCLM) and an overall survival (OS).

Forty-three (43) patients with proven CRCLM were included, with the following criteria: MRI with delayed phase post contrast less than 3 months before metastasis resection; and HGP subtype classification on pathology (desmoplastic/non-desmoplastic). Non-desmoplastic growth patterns have a poor prognosis and may not benefit from anti VEGF-A therapy. Using system 100, each lesion was semi-automatically contoured in 3D, into an inner ROI representing lesion's inner core and a border ROI including 2 mm extension outside inner core. standard radiomics features (e.g., standard texture analysis features) were extracted for both ROIs: 6 global histograms (first order) and 22 second-order texture features, at three different levels of image smoothing. The curvature of isophotes was also computed by using system 100, and the six global histogram features were computed for each ROI on the curvature of isophote image. A Lasso logistic regression was used to fit three different models: (1) standard radiomics features and features from the curvature of isophotes; (2) standard radiomics features alone; (3) only features computed from the curvature of isophotes. These models were applied independently to the border and inner ROI.

A total of 69 CRCLM were segmented. Lesions with volumes <1.7 cm$^3$ were excluded, resulting in 43 lesions for final analysis: 25/43 (58%) desmoplastic, and 18/43 (42%) non-desmoplastic. No association between HGP and image features was found for the inner ROI. For the border ROI, HGP and standard radiomics features showed no correlation (models 1-2); a correlation was present with the features from the curvatures of isophotes (model 3), with an area of under the ROC curve of 0.69, 89% sensitivity and 75% specificity. A significant Pearson correlation coefficient was also found between the variance of isophote curvature for border ROI and OS ($r=-0.31$, $p=0.015$).

In conclusion, an analysis of the curvature of isophotes focused on lesions borders may help in predicting CRCLM HGP in a non-invasive manner and correlates with OS.

Experiment 3: Detection of Deep Myometrial Invasion in Endometrial Cancer

The purpose of this experiment was to assess the performance of the curvature of isophotes as an imaging marker for detecting deep myometrial invasion in endometrial cancer.

This retrospective study included 99 women (median age, 65 years) with endometrial carcinomas measuring greater than 1 cm in maximal diameter who underwent 1.5-T MR imaging before hysterectomy between 2011 and 2015.

The curvature of isophotes was computed by system 100 for each patient on two MRI sequences: dynamic contrast enhanced (DCE) and post-gadolinium (PG) delayed phase, and was then averaged over the lesion. The 99 patients were divided into two groups, based on presence or absence of deep myometrial invasion. The univariate group difference was then computed using a t-test.

With both sequences, the curvature of isophotes gave significant group differences: PG delayed phase: p=1.9e−4; DCE: p=0.0032.

Thus, the curvature of isophotes may be used to differentiate between the presence and absence of deep myometrial invasion in endometrial cancer.

The measurement extracted from the curvature map better differentiate myometrial invasion than the one performed on the non-post treated images.

Experiment 4: Mean Curvature of Isophotes—a Novel Quantitative CT Metric with Improved Discrimination Between Early Chronic Obstructive Pulmonary Disease (COPD) and Healthy Subjects Spirometry and quantitative CT scans (qCT) may discriminate poorly between early COPD and health. In this example, it is sought to measure the ability of the mean curvature of isophotes to do so. The mean curvature of isophotes (MCI) is specific to known aspects of image geometry, which is hypothesized to be important in capturing changes in lung parenchyma occurring early in COPD.

In the following, the performance of two standard qCT metrics, i.e., lung density (LD, 15th percentile LD histogram) and low attenuation area (LAA, % area LD histogram<−950 HU), are compared to the mean curvature of isophotes. Isophotes and their mean curvature are classical concepts in computer vision. However, to the inventor's knowledge they have not previously been applied to qCT. The MCI is computed using equation (1) above, where $\kappa$ corresponds to MCI, I is the image and $\nabla$ is the gradient operator. The MCI-derived metric described herein was computed using in-house software. The LAA and LD were computed using the Chest Imaging Platform software (chestimagingplatform.org). 251 subjects were studied included healthy controls (n=29, asymptomatic, FEV1/FVC>0.7), non-GOLD COPD (n=26, symptomatic, >10 pack-years smoking, FEV1/FVC>0.7, and either MMEF<65% or RV>130% predicted) and GOLD COPD spirometric stages I-IV (n=33, 106, 46, 11, respectively). GOLD stands for the Global Initiative for Chronic Obstructive Lung Disease (www.goldcopd.org), a consortium of experts that develops guidelines for management and classification (staging) of COPD. GOLD stages I-IV COPD were grouped together to collapse subjects into 3 groups. Pairwise classification experiments between each pair of groups were performed, for each of the 3 metrics under consideration. For each such pairwise classification, a receiver operating characteristic (ROC) curve is computed, from which the area-under-the-curve (AUC) and Youden's index was derived. Youden's index defines an optimal cut-off point along the ROC curve, for which sensitivity, specificity and positive and negative predictive values are reported. 95% confidence intervals (CI) were estimated using the bootstrap method with 2000 samples.

In this experiment, it is observed that that LD and LAA performed comparably to MCI when the comparison involved GOLD I-IV subjects. However, MCI can discriminate better between healthy controls and non-GOLD COPD, compared to LD and LAA (see results in Table 1). In this example, it was shown that the MCI metric presented herein can perform better than classical qCT metrics discriminating between healthy control and early stage COPD subjects. If confirmed in larger independent populations, CT scans could potentially identify COPD subjects at an earlier stage of disease than spirometry.

Figure 14A:
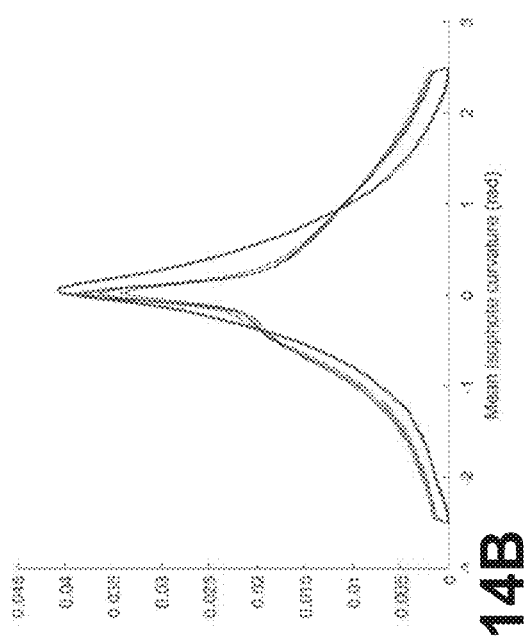
FIGS. 14A-H are graphs showing mean curvatures of isophotes for different 3D anatomical images of lungs of patients, in which the graph of FIG. 14A is associated to a healthy patient, the graph of FIG. 14B is associated to a patient diagnosed with interstitial lung disease (ILD), the graph of FIG. 14C is associated to a patient diagnosed with chronic obstructive pulmonary disease (COPD) and ILD, the graph of FIG. 14D is associated to a patient diagnosed with COPD IV, the graph of FIG. 14E is associated to a patient diagnosed with COPD III, the graph of FIG. 14F is associated to a patient diagnosed with COPD II, the graph of FIG. 14G is associated to a patient diagnosed with COPD I, and the graph of FIG. 14H is associated to a patient diagnosed with asthma, in accordance with one or more embodiments.
Figure 14B:
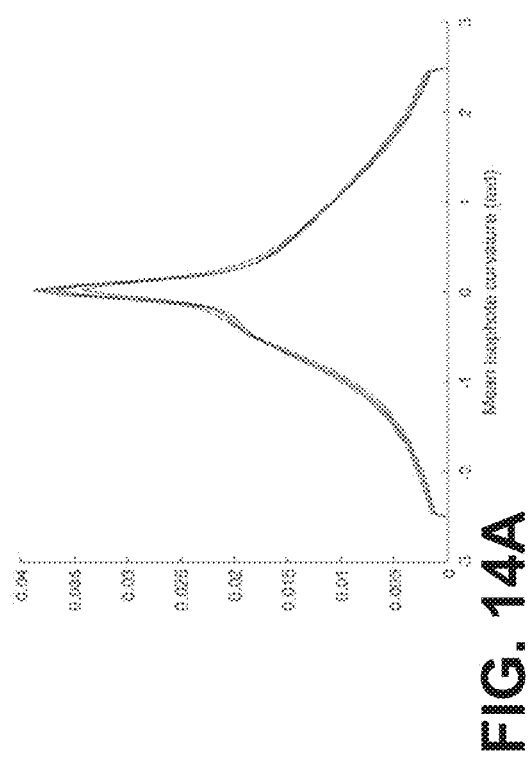
Figure 14C:
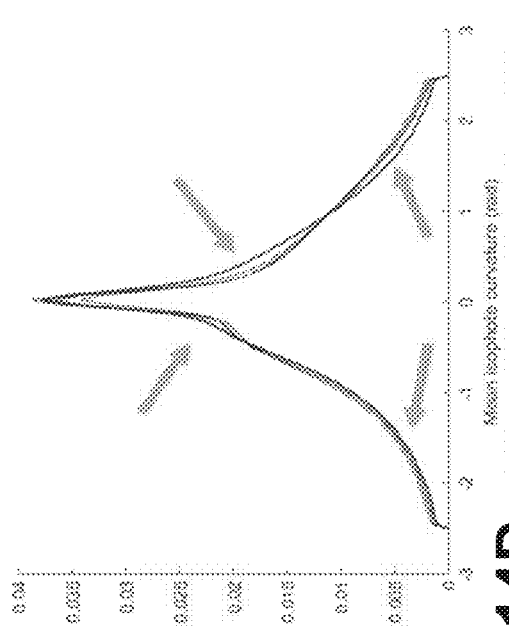
Figure 14D:
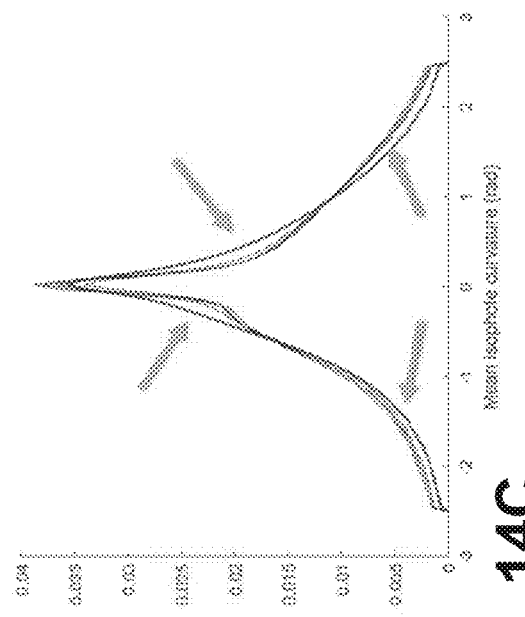
Figure 14E:
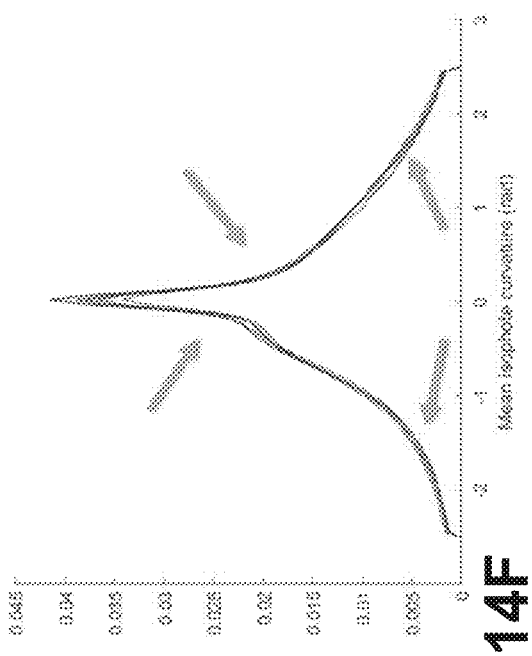
Figure 14F:
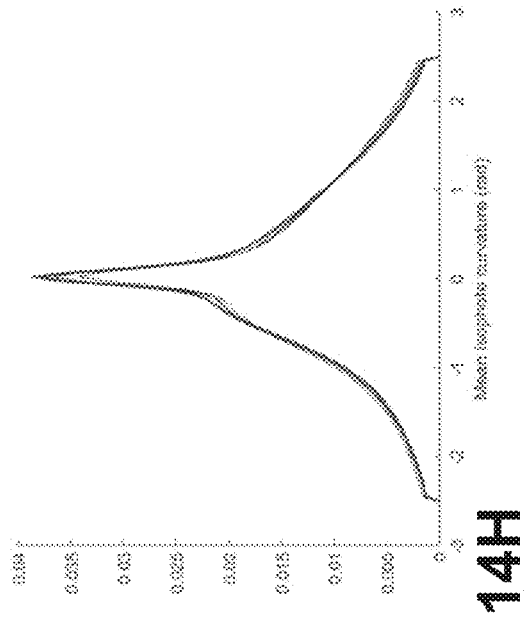
Figure 14G:
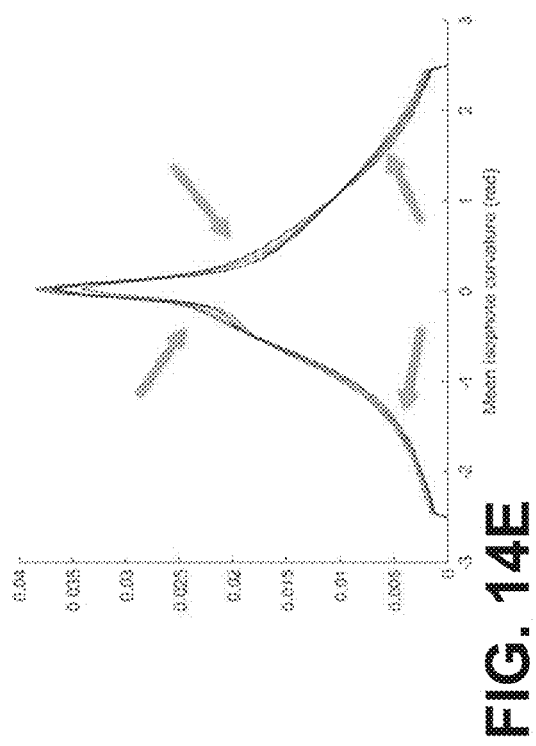
Figure 14H:
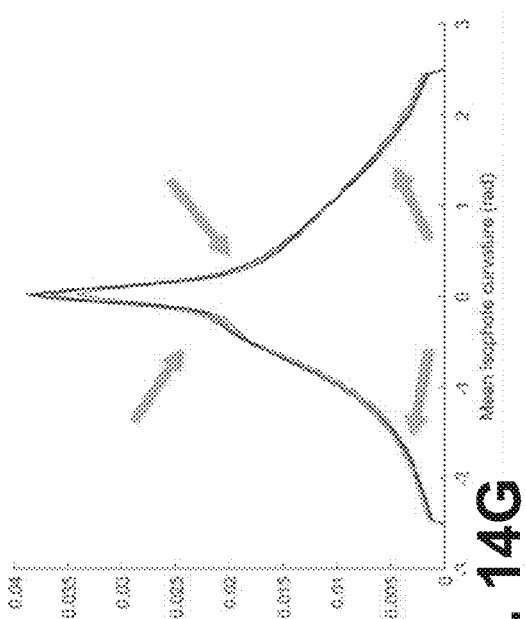

FIGS. 14A-H show graphs showing mean curvatures of isophotes for different 3D anatomical images of lungs of patients. More specifically, the graph of FIG. 14A is associated to a healthy patient, the graph of FIG. 14B is associated to a patient diagnosed with interstitial lung disease (ILD), the graph of FIG. 14C is associated to a patient diagnosed with chronic obstructive pulmonary disease (COPD) and ILD, the graph of FIG. 14D is associated to a patient diagnosed with COPD IV, the graph of FIG. 14E is associated to a patient diagnosed with COPD III, the graph of FIG. 14F is associated to a patient diagnosed with COPD II, the graph of FIG. 14G is associated to a patient diagnosed with COPD I, and the graph of FIG. 14H is associated to a patient diagnosed with asthma.

Table 1 below presents discriminatory measures of mean curvature of isophotes, LD and LAA for early COPD.

| Healthy Controls vs. Non-GOLD COPD | MCI | (95% CI) | LD | (95% CI) | LAA | (95% CI) |
| --- | --- | --- | --- | --- | --- | --- |
| AUC | 0.76 | (0.59-0.87) | 0.50 | (0.50-0.51) | 0.59 | (0.50-0.73) |
| Sensitivity | 0.73 | (0.54-1.00) | 0.85 | (0.46-1.00) | 0.30 | (0.10-0.38) |
| Specificity | 0.74 | (0.23-0.83) | 0.33 | (0.11-0.39) | 0.92 | (0.73-1.00) |
| Positive Predictive Value | 0.73 | (0.51-0.84) | 0.55 | (0.36-0.64) | 0.80 | (0.59-1.00) |
| Negative Predictive Value | 0.74 | (0.58-0.91) | 0.69 | (0.50-1.00) | 0.56 | (0.29-0.67) |
| Youden's Index | 0.47 | (0.19-0.62) | 0.18 | (0.08-0.23) | 0.22 | (0.08-0.35) |

In conclusion, an analysis of the curvature of isophotes focused on lung condition can help determine a medical condition diagnosis of the type of medical condition and/or of the severity of the condition.

Experiment 5: Liver Tumors—Prediction of Treatment

A study included 47 patients with liver tumors that underwent a particular kind of treatment called trans-arterial chemoembolization (TACE). Imaging was done before treatment, as well as after treatment. On the pre-treatment images, the tumors were segmented as described in the present disclosure. Mean Curvature of Isophotes (MCI) images were computed. Within the segmented tumor region, a histogram of MCI values was constructed, and six features were computed from this histogram: mean, variance, kurtosis, skewness, uniformity, entropy. Treatment outcome was assessed by a radiologist on the post-treatment images. Based on this outcome, patients were categorized into one of two groups: good response, and bad response. A machine-learning classifier algorithm (e.g., involving random forests) was trained on the pre-treatment MCI images. Using bootstrapping to assess classification performance on the same training set, the method achieved an average prediction accuracy of 0.72.

The methods and systems described herein may be implemented in a high level procedural or object oriented programming or scripting language, or a combination thereof, to communicate with or assist in the operation of a computer system, for example the computing device 1100. Alternatively, the methods and systems described herein may be implemented in assembly or machine language. The language may be a compiled or interpreted language. Program code for implementing the methods and systems described herein may be stored on a storage media or a device, for example a ROM, a magnetic disk, an optical disc, a flash drive, or any other suitable storage media or device. The program code may be readable by a general or special-purpose programmable computer for configuring and operating the computer when the storage media or device is read by the computer to perform the procedures described herein. Embodiments of the methods and systems described herein may also be considered to be implemented by way of a non-transitory computer-readable storage medium having a computer program stored thereon. The computer program may comprise computer-readable instructions which cause a computer, or more specifically the at least one processing device of the computer, to operate in a specific and pre-defined manner to perform the functions described herein.

Computer-executable instructions may be in many forms, including program modules, executed by one or more computers or other devices. Generally, program modules include routines, programs, objects, components, data structures, etc., that perform particular tasks or implement particular abstract data types. Typically the functionality of the program modules may be combined or distributed as desired in various embodiments.

Various aspects of the methods and circuits for the system 100 disclosed herein may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments. Although particular embodiments have been shown and described, it will be obvious to those skilled in the art that changes and modifications may be made without departing from this invention in its broader aspects. The scope of the following claims should not be limited by the preferred embodiments set forth in the examples, but should be given the broadest reasonable interpretation consistent with the description as a whole.

Embodiments of methods, systems, and apparatus herein are described through reference to the drawings.

The embodiments of the devices, systems and methods described herein may be implemented in a combination of both hardware and software. These embodiments may be implemented on programmable computers, each computer including at least one processor, a data storage system (including volatile memory or non-volatile memory or other data storage elements or a combination thereof), and at least one communication interface.

Program code is applied to input data to perform the functions described herein and to generate output information. The output information is applied to one or more output devices. In some embodiments, the communication interface may be a network communication interface. In embodiments in which elements may be combined, the communication interface may be a software communication interface, such as those for inter-process communication. In still other embodiments, there may be a combination of communication interfaces implemented as hardware, software, and combination thereof.

Throughout the foregoing discussion, numerous references will be made regarding servers, services, interfaces, portals, platforms, or other systems formed from computing devices. It should be appreciated that the use of such terms is deemed to represent one or more computing devices having at least one processor configured to execute software instructions stored on a computer readable tangible, non-transitory medium. For example, a server can include one or more computers operating as a web server, database server, or other type of computer server in a manner to fulfill described roles, responsibilities, or functions.

The technical solution of embodiments may be in the form of a software product. The software product may be stored in a non-volatile or non-transitory storage medium, which can be a compact disk read-only memory (CD-ROM), a USB flash disk, or a removable hard disk. The software product includes a number of instructions that enable a computer device (personal computer, server, or network device) to execute the methods provided by the embodiments.

The embodiments described herein are implemented by physical computer hardware, including computing devices, servers, receivers, transmitters, processors, memory, displays, and networks. The embodiments described herein provide useful physical machines and particularly configured computer hardware arrangements.

Although the embodiments have been described in detail, it should be understood that various changes, substitutions and alterations can be made herein.

Moreover, it is intended that the systems and methods described in this disclosure are not limited to monitor a patient post-cancer treatment. Rather, the systems and methods described herein can assess any other suitable condition. For instance, the systems and methods described herein can be used to assess a chronic disease such as with chronic obstructive pulmonary disease, also with interstitial lung disease.

Moreover, the scope of the present application is not intended to be limited to the particular embodiments of the process, machine, manufacture, composition of matter, means, methods and steps described in the specification.

As can be understood, the examples described above and illustrated are intended to be exemplary only. The scope is indicated by the appended claims.

What is claimed is:

1. A computer-implemented method of performing medical treatment outcome assessment or medical condition diagnostic, the method comprising:
   receiving a three-dimensional (3D) anatomical image representing a region of a body of a patient;
   generating a 3D invariant image by processing the 3D anatomical image based on an isophote structure invariant entity;
   using an image processing unit, generating an output based on said 3D invariant image, the output being either:
      medical treatment outcome data indicative of an outcome assessment of a treatment received by said patient; or
      medical condition diagnostic data indicative of a diagnostic of a medical condition of said patient.

2. The method of claim 1 wherein said isophote structure invariant entity is a mean curvature of isophotes.

3. The method of claim 2 wherein an isophote is represented with an equation I(x,y,z)=c, wherein I represents the image, x, y and z are variables representing 3D spatial coordinates, and c is a constant.

4. The method of claim 3 wherein the mean curvature of isophotes κ is computed based on the formula $$\kappa = div\left(\frac{\nabla I}{\|\nabla I\|}\right),$$

in which $$div\left(\frac{\nabla I}{\|\nabla I\|}*\right)$$

represents the divergence of the quantity $$\frac{\nabla I}{\|\nabla I\|}*,$$

$\nabla I$ represents the gradient of the image I and is given by $\nabla I=(I_x,I_y,I_z)$ with $I_x$, $I_y$ and $I_z$ corresponding to first-order derivatives of the image I along corresponding 3D spatial coordinates, and $\|\nabla I\|$ represents the magnitude of the gradient of the image I and is given by $\|\nabla I\|=(I_x^2+I_y^2+I_z^2)^{1/2}$.

5. The method of claim 1 wherein the isophote structure invariant entity is a first isophote structure invariant entity and the 3D invariant image is a first 3D invariant image, the method further comprising generating a second 3D invariant image by processing the 3D anatomical image based on a second isophote structure invariant entity different from the first isophote structure invariant entity, said generating said output being based on the first and second 3D invariant images.

6. The method of claim 5 further comprising wherein the first isophote structure invariant entity is a mean curvature of isophotes and the second isophote structure invariant entity is a Gaussian curvature of isophotes.

7. The method of claim 1 further comprising receiving data representative of treatment received by the patient, said generating said output being based on the 3D invariant data and on said data representative of treatment received by the patient.

8. The method of claim 1 wherein the image processing unit is a trained image processing unit.

9. The method of claim 1 wherein the 3D anatomical image comprises: a computed tomography (CT) image, a magnetic resonance imaging (MRI) image, a positron emission tomography (PET) scan image, or an ultrasound image.

10. The method of claim 1 further comprising displaying said output via a user interface.

11. A system for performing medical treatment outcome assessment or medical condition diagnostic, the system comprising:
    a processing device; and
    a non-transitory memory communicatively coupled to the processing device and comprising computer-readable program instructions executable by the processing device for:
      receiving a three-dimensional (3D) anatomical image representing a region of a body of a patient;
      generating a 3D invariant image by processing the 3D anatomical image based on an isophote structure invariant entity;
      using an image processing unit, generating an output based on said 3D invariant image, the output being either:
        medical treatment outcome data indicative of an outcome assessment of a treatment received by said patient; or
        medical condition diagnostic data indicative of a diagnostic of a medical condition of said patient.

12. The system of claim 11 wherein said isophote structure invariant entity is a mean curvature of isophotes.

13. The system of claim 12 wherein an isophote is represented with an equation I(x,y,z)=c, wherein I represents the image, x, y and z are variables representing 3D spatial coordinates, and c is a constant.

14. The system of claim 13 wherein the mean curvature of isophotes κ is computed based on the formula $$\kappa = div\left(\frac{\nabla I}{\|\nabla I\|}\right),$$

in which $$div\left(\frac{\nabla I}{\|\nabla I\|}*\right)$$

represents the divergence of the quantity $$\frac{\nabla I}{\|\nabla I\|}*, \nabla I$$

represents the gradient of the image I and is given by $\nabla I=(I_x,I_y,I_z)$ with $I_x$, $I_y$ and $I_z$ corresponding to first-order derivatives of the image I along corresponding 3D spatial coordinates, and $\|\nabla I\|$ represents the magnitude of the gradient of the image I and is given by $\|\nabla I\|=(I_x^2+I_y^2+I_z^2)^{1/2}$.

15. The system of claim 11 wherein the isophote structure invariant entity is a first isophote structure invariant entity and the 3D invariant image is a first 3D invariant image, the method further comprising generating a second 3D invariant image by processing the 3D anatomical image based on a second isophote structure invariant entity different from the first isophote structure invariant entity, said generating said output being based on the first and second 3D invariant images.

16. The system of claim 15 further comprising wherein the first isophote structure invariant entity is a mean curvature of isophotes and the second isophote structure invariant entity is a Gaussian curvature of isophotes.

17. The system of claim 11 further comprising receiving data representative of treatment received by the patient, said generating said output being based on the 3D invariant data and on said data representative of treatment received by the patient.

18. The system of claim 11 wherein the image processing unit is a trained image processing unit.

19. The system of claim 11 wherein the 3D anatomical image comprises: a computed tomography (CT) image, a magnetic resonance imaging (MRI) image, a positron emission tomography (PET) scan image, or an ultrasound image.

20. The system of claim 11 further comprising a user interface communicatively coupled to said processing device displaying said output.

21. A computer-implemented method for computing an imaging marker to monitor a patient treatment, the method comprising:
receiving an image representing a region of a body of a patient;
processing the image based on an isophote structure invariant entity of the image;
computing a data set representative of the isophote structure invariant entity;
receiving data representative of the patient treatment received by the patient;
determining a likelihood of success of the patient treatment received by the patient based on the data set representative of the isophote structure invariant entity and the data representative of the patient treatment; and
generating a signal based on said determined likelihood of success.

22. The method of claim 21 wherein the patient treatment is a post-cancer treatment.

23. The method of claim 21 wherein the isophote structure invariant entity is a mean curvature of isophotes.

* * * * *